US009273304B2

(12) United States Patent
Lagunavicius et al.

(10) Patent No.: US 9,273,304 B2
(45) Date of Patent: Mar. 1, 2016

(54) INACTIVATION METHOD

(75) Inventors: Arunas Lagunavicius, Vilnius (LT); Daiva Tauraite, Vilnius (LT); Jurgita Barkauskaite, Vilnius (LT); Leonas Grinius, Vilnius (LT)

(73) Assignee: Thermo Fisher Scientific Baltics UAB, Vilnius (LT)

( * ) Notice: Subject to any disclaimer, the term of this patent is extended or adjusted under 35 U.S.C. 154(b) by 1495 days.

(21) Appl. No.: 11/649,819

(22) Filed: Jan. 5, 2007

(65) Prior Publication Data

US 2007/0224611 A1    Sep. 27, 2007

(30) Foreign Application Priority Data

Jan. 6, 2006 (GB) .................................. 0600228.1

(51) Int. Cl.
| C12N 9/99 | (2006.01) |
| C07D 207/404 | (2006.01) |
| C07D 209/48 | (2006.01) |
| C12N 9/12 | (2006.01) |

(52) U.S. Cl.
CPC .............. *C12N 9/99* (2013.01); *C07D 207/404* (2013.01); *C07D 209/48* (2013.01); *C12N 9/1252* (2013.01)

(58) Field of Classification Search
CPC .... C12N 9/99; C12N 9/1252; C07D 207/404; C07D 209/48
See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,965,188 | A | 10/1990 | Mullis et al. |
| 5,338,671 | A | 8/1994 | Scalice et al. |
| 5,411,876 | A | 5/1995 | Bloch et al. |
| 5,677,152 | A | 10/1997 | Birch et al. |
| 5,773,258 | A | 6/1998 | Birch et al. |
| 6,183,998 | B1 | 2/2001 | Ivanov et al. |
| 6,335,179 | B1 | 1/2002 | Short |
| 6,479,264 | B1 | 11/2002 | Louwrier |
| 2002/0193367 | A1* | 12/2002 | Adam et al. ................... 514/221 |

FOREIGN PATENT DOCUMENTS

| EP | 0 462 808 A3 | 12/1991 |
| EP | 0 771 870 A1 | 5/1997 |
| GB | 2 162 177 A | 1/1986 |
| WO | WO 2005/123913 | 12/2005 |

OTHER PUBLICATIONS

Ishikawa et al. J. Jpn. Oil Chem. Soc. (Yakagaku) (1989) 38(1): 60-64.*
Keller et al. Helvetica Chimica Acta (1975) 58(62-63): 531-541.*
Lawyer et al. J. Biol. Chem. (1989) 264(11): 6427-2437.*
Patani et al. Chem. Rev. (1996) 96: 3147-3176.*
Kaehler, M et al: "Cloning and Characterization of a Family B DNA Polymerase from the Hyperthermophilic Crenarchaeon Pyrobaculm Islandicum." Journal of Bacteriology, Feb. 2000 pp. 655-663.
Ryan, Orlaith et al: "Thermostabilized Chemical Derivatives of Horseradish Peroxidase" Enzyme and Microbial Technology, vol. 16, No. 6, 1994, pp. 501-505.
Wasylyk, B et al: Chemical Modification of Ribonucleic Acid Polymerase with N Bromosuccinimide Biochemical Society Transactions, 1975, vol. 3, No. 5, 1975, p. 654.
Keller, O et al: "Preparation and Some Properties of Maleimido Acids and Maleoyl Derivatives of Peptides" Helvetuca Chimica Acta, Verlag Helvetica Chimica Acta, Basel, Ch, vol. 58, No. 62/63, Mar. 12, 1975, pp. 531-541.
Andruszkiewicz, R et al: "Structural Derterminants of Inhibitory Activity of N3-(4-Methoxyfumaroyl)-L-2,3-Diaminopropanoic Acid Towards Glucosamine-6-Phosphate Synthase" Polish Journal of Chemistry, Polish Chemical Society, vol. 67, No. 4, Apr. 1993, pp. 673-683.
Lehmann, Guenter et al: "Reaction of N-Ethoxycarbonylsuccinimide with Amines" Justus Liebigs Annalen Der Chemie, Verlag Chemie GmbH, Weinheim, DE, vol. 754, No. 1, Jan. 26, 1972, pp. 154-156.
Palacian, E et al: "Dicarboxylic Acis Anhydrides As Dissociating Agents of Protein-Containing Structures" Molecular and Cellular Biochemistry, Norwell, MA, US, vol. 97, No. 2, 1990, pp. 101-111.
European Search Report dated Oct. 17, 2007 (Seven (7) pages).
Quin Chou et al., "Prevention of Pre-PCR Mis-Priming and Primer Dimerization Improves Low-Copy-Number Amplifications", Nucleic Acids Research, Feb. 25, 1992, pp. 1717-1723, vol. 20, No. 7, 1992 Oxford University Press.
Matthew J. Cuneo et al., "The Backbone Structure of the Thermophilic Thermoanaerobacter Tengcongensis Ribose Binding Protein is Essentially Identical to its Mesophilic *E. coli* Homolog", BMC Structural Biology, Mar. 28, 2008, pp. 1-11, vol. 8, No. 20, BioMed Central.
D. Georlette et al., "A DNA Ligase from the Psychrophile Pseudoalteromonas Haloplanktis Gives Insights into the Adaptation of Proteins to Low Temperatures", Eur. J. Biochem., 2000, pp. 3502-3512, vol. 267, FEBS 2000.
Daphné Georlette et al., "Structural and Functional Adaptations to Extreme Temperatures in Psychrophilic, Mesophilic, and Thermophilic DNA Ligases", The Journal of Biological Chemistry, Sep. 26, 2003, pp. 37015-37023, vol. 278, No. 39, The American Society of Biochemistry and Molecular Biology, Inc., USA.
D. Georlette et al., "Some Like it Cold: Biocatalysis at Low Temperatures", FEMS Microbiology Reviews, 2004, pp. 25-42, vol. 28, Elsevier Science B.V.
Georges Feller et al., "Psychrophilic Enzymes: Hot Topics in Cold Adaptation", Nature Reviews, Dec. 2003, pp. 200-208, vol. 1.
M. Kawai et al., "RNA Polymerase Mutants of *Escherichia coli*", Molec. Gen. Genet., 1976, pp. 233-241, vol. 143, Springer-Verlag, XP008101100.

(Continued)

*Primary Examiner* — Susan Hanley
(74) *Attorney, Agent, or Firm* — Crowell & Moring LLP

(57) ABSTRACT

The present invention relates to the field of thermostable enzymes, methods for their inactivation, and related uses, kits and reagents. In particular, the invention relates to a method for reversible inactivation of thermophilic enzymes by chemical modification under aqueous or non-aqueous conditions.

15 Claims, 15 Drawing Sheets

(56) References Cited

OTHER PUBLICATIONS

G.H.L. Nefkens et al., "A Simple Preparation of Phthaloyl Amino Acids Via a Mild Phthaloylation" Recueil, 1960, pp. 688-698, vol. 79.

Ashley Parker, "Formation of Imides from Anhydrides; 2,3-Dimethylmaleimide", Synthetic Page, Mar. 7, 2002, p. 1 of 1, vol. 185.

Randall K. Saiki et al., "Enzymatic Amplification of β-Globin Genomic Sequences and Restriction Site Analysis for Diagnosis of Sickle Cell Anemia", Science, Dec. 20, 1985, pp. 1350-1354, vol. 230.

J. Trujillo-Ferrara et al., "Reversible and Irreversible Inhibitory Activity of Succinic and Maleic Acid Derivatives on Acetylcholinesterase" European Journal of Pharmaceutical Sciences, 2003, pp. 313-322, vol. 18, Elsevier Science B.V., XP007906940.

Paul M. Worster et al., "N-(Ethoxycarbonyl)phthalimide. An Improved Procedure." J. Org. Chem., 1980, pp. 174-175, vol. 45, 1980 American Chemistry Society.

"HotStarTaq PCR Handbook: for HotStartTaq DNa Polymerase/ HotStarTaq Master Mix Kit", Nov. 2002, Qiagen Worldwide, pp. 1-36.

A. Makioka et al., "Detection and Characterization of DNA Polymers Activity in Entamoeba Histolytica", Parasitol Res, vol. 82, pp. 87-89, 1996.

Khosro Khajeh, et al., "Chemical modification of lysine residues in *Bacillus* α-*amylases*: effect on activity and stability", Enzyme and Microbial Technology, Apr. 5, 2001, pp. 543-549, vol. 28, No. 6.

AmpliTaq Gold Manual, http://tools.lifetechnologies.com/content/sfs/manuals/cms_041554.pdf, 2000, pp. 1-16.

* cited by examiner

General formula of modificator

Y : dicarboxylic acid residue ;

A  X : H ;

B  X : electron withdrawing group

Figure 6. Example of reversible modification

Chemical Hot-start DNA polymerases

Fast PCR

95°C-30 s;
(95°C-0 s, 62°C-12 s) 30 cycles;
72°C-10 s.

[Human DNA] – 40 ng / 20 µl
[Polymerase] – 1 u / 20 µl

1 - Taq DNA polymerase;
2 – Modified Taq DNA polymerase;
3 - "HotStarTaq DNA polymerase" (Qiagen);
4 - "AmpliTaq Gold DNA polymerase" (Applied Biosystems);
5 - "FastStart Taq DNA polymerase" (Roche).

INACTIVATION METHOD

FIELD OF THE INVENTION

The present invention relates to the field of thermostable enzymes, methods for their inactivation, and related uses, kits and reagents. In particular, the invention relates to a method for reversible inactivation of thermophilic enzymes by chemical modification under aqueous or non-aqueous conditions. There is a constant demand in the industry for chemically modified thermophilic enzymes with superior characteristics for applications in the field of molecular biology, including nucleic acid amplification by PCR.

BACKGROUND OF THE INVENTION

One of the main nucleic acid amplification techniques is the Polymerase Chain Reaction (PCR) (Saiki et al., Science, 230:1350-54 (1985)) taught in U.S. Pat. Nos. 4,683,202; 4,683,195; and 4,965,188, each incorporated herein by reference. Many commercial suppliers, including Fermentas, offer reagents for PCR.

PCR reaction mixture is basically assembled from the following components: nucleic acid target template, two or several target-specific oligonucleotides (primers), a thermophilic nucleic acid polymerase, deoxyribonucleoside triphosphates and a reaction buffer.

In each cycle of PCR amplification, a double-stranded target sequence is denatured, primers are annealed to each strand of the denatured target, and the primers are extended by the action of a DNA polymerase. DNA synthesis initiates at the accessible 3'-OH group of the target-specific oligonucleotides flanking the DNA sequence to be copied, thereby generating an identical copy of the target template nucleic acid sequence. The enzymatic reaction is repeated for a substantial number of thermal cycles consisting of the denaturation of the target nucleic acid, annealing of the primer oligonucleotides to complementary nucleic acid sequences and the subsequent extension of these primer-template complexes by the thermophilic nucleic acid polymerase.

Specificity of DNA amplification depends on the specificity of primer hybridization. Oligonucleotide primers for PCR are designed to be complementary to, or substantially complementary to, sequences occurring at the 3' end of each strand of the target nucleic acid sequence. Hybridization of the primers with the target occurs usually at sufficiently high temperature to provide annealing conditions that ensure binding of the primers mainly to the complementary nucleic acid sequence of the target. However, PCR reaction mixtures are often assembled at room temperature, thus under less stringent oligonucleotide hybridization conditions. At room temperature, most thermophilic nucleic acid polymerases used for PCR possess a residual catalytic activity, which may cause degradation of primers and the formation of non specific byproducts, such as dimmers of primers or non-specific primer extension products. These unspecific PCR products can compete during subsequent PCR cycles with the specific PCR product for the primer molecules, DNA polymerase and nucleotides, thereby severely decreasing the efficiency of the amplification of the desired sequence (see, Chou et al., Nucleic Acids Research, 20(7): 1717-1723 (1992)).

A number of laborious, expensive and time-consuming approaches have been proposed to overcome difficulties related to the appearance of unspecific PCR byproducts. These so called "Hot Start" methods include physically separating reactants until annealing temperatures are reached, either manually ("manual hot-start PCR"), or by using wax (U.S. Pat. No. 5,411,876). Such procedures add a lot of extra time into the experimental process, and they also carry a higher risk of contamination due to the wax barrier itself or the requirement of opening the reaction vessel once some of the reactants have already been mixed and heated. Moreover, the formation of solid wax-barrier above the reaction mixture after finishing the PCR is less convenient for further sample processing.

Another method of reducing formation of unspecific extension products is a reversible inhibition of the DNA polymerase used in PCR. U.S. Pat. No. 5,338,671 discloses non-covalent modification of the nucleic acid polymerase by use of antibodies specific for said polymerase to inhibit the polymerase's activity. Pre-mixing of nucleic acid polymerase and polymerase-specific antibodies at room temperature results in the formation of antibody-polymerase complexes. Under these conditions, substantially no oligonucleotide extension by the DNA polymerase can be detected. At elevated temperatures, the antibodies become denatured and they dissociate from the complex, thereby releasing the active DNA polymerase. However, this method is expensive and carries the risk of contamination due to the possible presence of residual nucleic acids derived from the antibody preparation.

Several technologies for reversible covalent chemical inactivation of DNA polymerase, which becomes active only after incubation for a certain time period at elevated temperature, thus preventing production of PCR byproducts during the reaction set-up and the initial heating phase, are known in the prior art. It is generally considered that reversible chemical modification of DNA polymerase is the most convenient and preferred method for the "hot start" technique. Various modifying agents and modification conditions have been proposed that generate reversibly inactivated DNA polymerase with differing enzymatic characteristics that may be classified into two major groups of the modifying compounds:

1. protein acylation with dicarboxylic acid anhydrides (water based or organic solvent based reaction mixtures);
2. Protein modification with aldehydes resulting in the formation of Schiff bases.

The chemically modified DNA polymerase disclosed in U.S. Pat. Nos. 5,677,152, 5,773,258, which are incorporated herein in their entirety by reference, is prepared in a single phase water-based system by treating the enzyme with the modifying reagent, dicarboxylic acid anhydride. However, this method requires quite strict control of the reaction conditions, such as pH, temperature and the reagent excess.

Alternative approach was disclosed in the U.S. Pat. No. 6,479,264, where dicarboxylic acid anhydride was used as a modifying reagent and the reaction was carried out in an anhydrous aprotic organic solvent.

Aldehydes, preferably the formaldehyde, are another group of modifying reagents that reversibly inactivate the thermophilic enzymes under essentially aqueous conditions, as taught in the U.S. Pat. No. 6,183,998. However, thermophilic DNA polymerase obtainable by such a modification is characterised by comparatively long reactivation times, up to 15 minutes at 94° C., what is sometimes undesirable for experimental purposes.

SUMMARY OF THE INVENTION

Accordingly, the present invention provides a method for inactivating a thermostable enzyme, comprising reacting the enzyme with a dicarboxylic acid imide.

In a further aspect, the present invention provides an inactivated thermostable enzyme obtainable by a method as defined above.

In a further aspect, the present invention provides a dicarboxylic acid imide-derivatised thermostable enzyme.

In a further aspect, the present invention provides a method for amplifying a nucleic acid sequence, comprising: a) contacting a dicarboxylic acid imide-derivatised nucleic acid polymerase with the nucleic acid sequence at a first temperature in a reaction mixture, wherein the derivatised nucleic acid polymerase is at least partially inactivated at the first temperature; b) heating the reaction mixture to a second temperature higher than the first temperature, thereby reactivating the nucleic acid polymerase; c) amplifying the nucleic acid sequence in the reaction mixture by means of the reactivated nucleic acid polymerase.

In a further aspect, the present invention provides use of a dicarboxylic acid imide for inactivating a thermostable enzyme.

In a further aspect, the present invention provides use of a dicarboxylic acid imide-derivatised nucleic acid polymerase for amplifying a nucleic acid sequence.

In a further aspect, the present invention provides a kit comprising a dicarboxylic acid imide-derivatised thermostable nucleic acid polymerase and one or more components for performing a nucleic acid amplification reaction.

In a further aspect, the present invention provides a reaction mixture comprising a dicarboxylic acid imide-derivatised nucleic acid polymerase and one or more components for performing a nucleic acid amplification reaction.

In a further aspect, the present invention provides a compound of formula I:

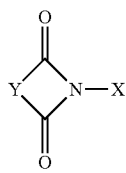

wherein:
X is halogen, hydroxyl, alkoxycarbonyl, alkoxy, acyl or acyloxy;
Y represents a radical of formula IIa or IIb;

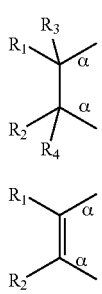

wherein:
$R_1$, $R_2$, $R_3$ and $R_4$ are each independently hydrogen or alkyl; or $R_1$ and $R_2$ together with the carbon atoms to which they are attached form a cycloalkylene, cycloalkenylene, cycloalkynylene or arylene group;
and each α is a bond linking the radical to a carbon atom of a carbonyl group shown in formula I.

The present invention provides novel methods and reagents for inactivation of thermophilic enzymes using a chemical modification, preferably under aqueous conditions. In particular, the thermophilic enzymes of the present invention are reversibly modified in the presence of dicarboxylic acid imides. The modified thermophilic DNA polymerases of the invention do not show significant enzyme activity at room temperature, while their enzymatic activity is restored within a few minutes at higher temperature, e.g. above 50° C., preferably at temperatures of above 75° C., and most preferably at 95° C.

Another advantage of the disclosed method of enzyme modification is the phenomenon that enzymes obtained thereby tolerate a quite broad pH range in the reaction mixture used in a subsequent PCR reaction. This is important when choosing optimal reaction conditions for each particular case.

By "thermostable" or "thermophilic" it is meant that the enzyme is relatively stable to heat, i.e. that the catalytic activity of the enzyme is not substantially impaired by heating. As mentioned above, according to the present invention an enzyme can be reversibly inactivated, the inactivation being reversed by heating. Thus "thermostable" refers to the ability of the enzyme (i) to retain its catalytic activity when heated before inactivation with the modifying agent, or (ii) to regain or retain its catalytic activity when heated during or after removal of the modifying agent (i.e. following reactivation). Clearly according to the present invention, the activity of an inactivated thermostable enzyme will increase with heating as the inactivation is reversed, i.e. as the modifying agent is removed. Thus references to an "inactivated thermostable enzyme" mean that enzyme catalytic activity can be restored by heating, and do not mean that inactivation of the enzyme is stable with heating.

For instance, thermostable enzymes can withstand the high temperature incubation used to remove the modifier groups, e.g. above 50° C., preferably above 75° C., and most preferably 95° C., without suffering a substantial irreversible loss of activity. Thus typically the thermostable enzyme is also capable of withstanding the temperatures used in the denaturation stage of a PCR reaction (e.g. 90 to 100° C.). Preferably a thermostable enzyme may retain at least 75%, preferably 90%, of its catalytic activity following incubation for 15 minutes at 90° C. In this aspect, catalytic activity at a first (catalytic) temperature (e.g. 70° C.) following a period of incubation at the elevated temperature (90° C.) is compared to catalytic activity of the enzyme at the first temperature prior to the period of incubation at the elevated temperature.

Thermostable enzymes suitable for use in the present invention include thermostable DNA polymerases and thermostable DNA ligases. Preferably the enzyme is a Taq DNA polymerase or Pfu DNA polymerase.

In one embodiment, the dicarboxylic acid imide comprises a compound of formula I:

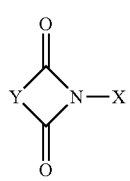

wherein:
X is hydrogen or an electron withdrawing group;
Y is a linker group.

By "electron withdrawing group" it is meant a group which can withdraw electron density from the N atom to which is bound, such that the electrophilicity and/or reactivity of one or both of the carbonyl carbon atoms in the dicarboxylic acid imide is increased, compared to when X is H. In other words, the presence of an electron withdrawing group shifts the shared electron pair in one or both of the N—C bonds in the compound towards the N atom, compared to when H is bound to the N atom.

Preferably X is hydrogen, halogen, hydroxyl, alkoxycarbonyl, alkoxy, acyl or acyloxy. More preferably X is halogen, hydroxyl, $C_1$-$C_8$alkoxycarbonyl, $C_1$-$C_8$alkoxy, $C_1$-$C_8$alkylcarbonyl or $C_1$-$C_8$alkylcarbonyloxy. A skilled person could select further electron withdrawing groups suitable for use in further embodiments.

The linker group Y is not particularly limited, and primarily serves as a linker between the two carbonyl groups of the imide moiety, which is the reactive group directly involved in reacting with and modifying the enzyme. The Y group is typically derived from the dicarboxylic acid used to form the dicarboxylic acid imide, and thus the Y group together with the two carbonyl groups form a dicarboxylic acid residue in the compound of formula I.

Preferably Y is alkylene, alkenylene, alkynylene, a bivalent carbocyclic ring, or a bivalent heterocyclic ring, wherein alkylene, alkenylene, alkynylene, the carbocyclic ring, or the heterocyclic ring:

a) optionally comprises one or more heteroatoms independently selected from N, O and S;

b) is optionally modified with one or more substituents independently selected from the following groups: alkyl, alkenyl, alkynyl, alkoxy, alkoxyalkyl, alkoxycarbonyl, alkoxycarbonylalkyl, acyl, acyloxy, acyloxyalkyl, amino, alkylamino, carboxy, cyano, thiocyano, halogen, hydroxy, nitro, acylamino, aminocarbonyl, carboxyamino;

c) is optionally modified with one or more further substituents, attached either (i) to the same carbon atom or heteroatom, or (ii) to different carbon atoms or heteroatoms, wherein the further substituents, together with the carbon atoms or heteroatoms to which they are attached, form a carbocyclic ring, or a heterocyclic ring containing one or more heteroatoms independently selected from N, O and S.

In any group comprising an alkyl chain (e.g. alkyl, alkylene, alkoxy, alkoxyalkyl, alkoxycarbonyl, alkoxycarbonylalkyl, acyloxyalkyl or alkylamino), each alkyl chain may be branched or straight and is preferably $C_1$-$C_8$, more preferably $C_1$-$C_6$, most preferably $C_1$-$C_4$. Alkenyl and alkynyl are each independently preferably $C_2$-$C_8$, more preferably $C_2$-$C_6$, most preferably $C_2$-$C_4$.

In any group comprising an acyl moiety (e.g. acyl, acyloxy, acyloxyalkyl, acylamino), acyl is preferably alkanoyl, e.g. $C_1$-$C_8$, more preferably $C_1$-$C_6$, more preferably $C_1$-$C_4$ alkylcarbonyl.

A carbocyclic or heterocyclic ring preferably comprises 5 to 10 members, more preferably 5 to 7 members, of which 1 to 3 may be hetero atoms selected from N, O and S in the case of a heterocyclic ring.

Halogen is preferably fluoro, chloro, bromo or iodo.

In a preferred embodiment, Y is $C_{1-6}$alkylene, $C_{2-6}$alkenylene, a bivalent 5 to 10-membered carbocyclic ring or a bivalent 5 to 10-membered heterocyclic ring containing 1 to 3 heteroatoms selected from N, O and S;

wherein $C_{1-6}$alkylene, $C_{2-6}$alkenylene, the carbocyclic ring or the heterocyclic ring is optionally substituted by:

(a) one or more substituents independently selected from hydroxy, halogen, cyano, nitro, carboxy, $C_{1-8}$alkyl or $C_{1-8}$alkenyl, or (b) two substituents attached to adjacent carbon atoms, which together with the carbon atoms to which they are attached form a 5 to 10-membered carbocyclic ring or a 5 to 10-membered heterocyclic ring containing 1 to 3 heteroatoms selected from N, O and S.

In a more preferred embodiment, Y represents a radical of formula IIa or IIb:

wherein:

$R_1$, $R_2$, $R_3$ and $R_4$ are each independently hydrogen or alkyl;

or $R_1$ and $R_2$ together with the carbon atoms to which they are attached form a cycloalkylene, cycloalkenylene, cycloalkynylene or arylene group;

and each α is a bond linking the radical to a carbon atom of a carbonyl group shown in formula I.

In an embodiment, when Y represents a radical of formula IIb, at least one of $R_1$ and $R_2$ is alkyl.

In formula IIa or IIb, alkyl is preferably $C_1$-$C_4$alkyl and the cycloalkylene, cycloalkenylene, cycloalkynylene or arylene group comprises 5 to 7 members.

In a further preferred embodiment, the dicarboxylic acid imide is an N-alkoxycarbonyl-2,3-dimethylmaleinimide. More preferably the dicarboxylic acid imide is N—($C_1$-$C_4$) alkoxycarbonyl-2,3-dimethylmaleinimide, most preferably N-ethoxycarbonyl-2,3-dimethylmaleinimide.

In general, the dicarboxylic acid imides of formula I may be prepared by reacting a corresponding dicarboxylic acid, or dicarboxylic acid anhydride, with ammonia, a primary amine or an amide, for example urea. The electron-withdrawing group X may be incorporated into the dicarboxylic acid imide at this stage, for example where the dicarboxylic acid anhydride is reacted with an amide. Alternatively, the method may involve first reacting the dicarboxylic acid anhydride with ammonia or urea to produce a compound of formula I wherein X is H, and subsequently introducing the X group into the compound. For instance, where the electron-withdrawing group X is alkoxycarbonyl, a compound of formula I wherein X is H may be reacted with an alkylhaloformate, preferably alkylchloroformate.

The enzyme may be reacted with the dicarboxylic acid imide in an aqueous medium or in an aprotic medium, such as in organic solvent. Preferably the reaction takes place in an aqueous medium, for instance wherein the pH of the medium is from 8.0 to 9.0 at 25° C. The enzyme is typically reacted with the dicarboxylic acid imide for 1 to 40 hours at a temperature of 1 to 50° C. The enzyme may be mixed with the dicarboxylic acid imide in a reaction mixture, in a molar ratio of enzyme:imide of 1:20 to 1:1280, more preferably 1:20 to 1:200.

Inactivation of the enzyme is preferably reversible. Inactivation of the enzyme may be reversed by heating, for instance to a temperature of at least 50° C., more preferably 75 to 99° C., most preferably 90 to 99° C. The enzyme may be heated to this temperature for 15 seconds to 20 minutes, more preferably 30 seconds to 5 minutes.

Inactivation of the enzyme may also be reversed by changing, typically decreasing, the pH of a medium comprising the enzyme. Preferably the pH of the medium is dependent on temperature, such that when the medium is heated its pH decreases and the enzyme is reactivated. A particularly preferred medium is a buffer comprising tris(hydroxymethyl)methylamine.

Once the enzyme has been inactivated by the process described above, it may be immediately used e.g. in a PCR amplification method or other application in which it becomes reactivated. Alternatively, the inactivated enzyme may be stored, to be reactivated at a later time, provided that it is stored at a temperature of less than 50° C., preferably less than 30° C. If the inactivated enzyme is exposed to too high temperatures during storage, it may be prematurely reactivated. Preferably the enzyme is stored in an aqueous medium at a pH of 8.0 to 9.0.

Preferably the enzyme is then contacted with a substrate, while it is still in the inactivated state. When the enzyme is in its active state, it is capable of catalyzing a reaction involving the substrate. The present invention advantageously allows the enzyme to be contacted with its substrate, but without any reaction being catalysed, until it is decided to reverse inactivation of the enzyme. Thus the method typically comprises a further step of reversing inactivation of the enzyme in the presence of the substrate, for instance by heating the enzyme together with the substrate.

The dicarboxylic acid imide-derivatised thermostable enzyme of the present invention is preferably derivatised at one or more amino groups in the enzyme. The derivatised enzyme preferably comprises a moiety of formula IIIa or IIIb:

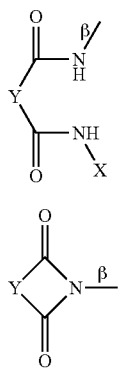

wherein X and Y are as defined above; and
β is a bond linking the moiety to the enzyme.

More preferably the enzyme is derivatised at a ε-amino group in a lysine residue in the enzyme, such that the enzyme comprises a derivatised lysine residue of formula IVa or IVb:

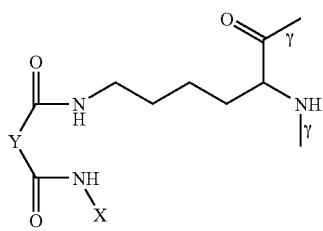

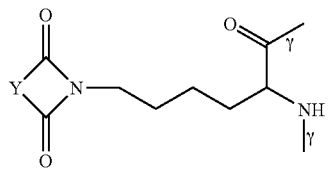

wherein X and Y are as defined above; and
each γ is a peptide bond linking the derivatised residue to an adjacent amino acid residue in a polypeptide chain of the enzyme.

Alternatively, the enzyme is derivatised at an α-amino group of an N-terminal amino acid residue in the enzyme.

Preferably the enzyme is derivatised at an amino acid residue involved in enzymatic catalysis, substrate recognition or determining structural conformation of the enzyme, for instance at an amino acid residue located at the active site of the enzyme.

Preferably the derivatised enzyme is at least partially inactivated. The activity of the derivatised enzyme is preferably at least 50% lower, more preferably at least 70% lower, than activity of an underivatised enzyme. Activity of the derivatised and underivatised enzyme may be compared at any suitable temperature, depending on the nature of the enzyme and its normal or optimum catalytic temperature, e.g. at a temperature of 70° C. or 25° C.

The method for amplifying a nucleic acid sequence of the present invention preferably comprises a further step of adding nucleic acid primers to the reaction mixture at the first temperature. Preferably the pH of the reaction mixture is 8.3 to 8.7, and the concentration of $Mg^{2+}$ ions in the reaction mixture is 1.5 to 5.0 mM.

Preferably step b) comprises a heating step as defined above. Step c) preferably comprises a polymerase chain reaction, and steps b) and c) are preferably performed in an automated thermocycler.

In step (c) the temperature of the reaction mixture is preferably varied over a repeated cycle, each cycle comprising 3 or more different temperatures stages. In this embodiment, each cycle comprises a denaturation stage at a third temperature, an annealing stage at a fourth temperature and an extension stage at a fifth temperature.

Alternatively step (c) may comprise a fast polymerase chain reaction, by which it is meant herein that each cycle consists of fewer than 3 different temperature stages (e.g. because annealing and extension stages are performed at the same temperature), and/or that the duration of each cycle is 30 seconds or less, preferably 15 seconds or less.

Preferably the polymerase chain reaction comprises 15 to 60 cycles.

The kit of the present invention preferably comprises one or more deoxynucleoside triphosphates, either separately as individual dNTPs or more preferably as a mixture of deoxyadenosine triphosphate, deoxyguanosine triphosphate, deoxythymidine triphosphate and deoxycytidine triphosphate.

In a preferred embodiment the kit additionally comprises a buffer solution, which particularly preferably comprises tris(hydroxymethyl)methylamine. The preferred pH of the buffer solution is 8.0 to 9.0 at 25° C.

Further preferred components of the kit are a solution comprising $Mg^{2+}$ ions, nucleic acid primers and a nucleic acid to be amplified in the polymerase chain reaction.

The reaction mixture of the present invention preferably comprises one or more components defined above as being comprised in the kit of the present invention. Whereas in the kit each component may be stored separately, e.g. in different vials, each component is found in admixture (e.g. in a single aqueous solution) in the reaction mixture of the present invention.

The kit and reaction mixture of the present invention preferably provide the necessary reagents for performing a polymerase chain reaction.

These and other aspects and advantages of the invention will be understandable for those skilled in the art from the description and examples presented below.

DETAILED DESCRIPTION OF THE INVENTION

1. Reversible Chemical Modification 1.1. Principle of Reversible Chemical Modification.

Chemical modification of protein comprises the modification object, which is a target protein, the modifying agent, the modified functional groups (the modification targets) of the protein, and the modification medium.

1. The preferred modification objects of this invention are the thermophilic enzymes, most preferred thermophilic DNA polymerases, e.g., Taq DNA polymerase or Pfu DNA polymerase.

Figure 1:
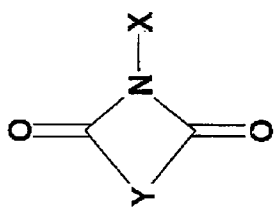
FIG. 1 shows a general formula for a preferred modifying agent according to the present invention. In art A of FIG. 1 group X is hydrogen. In part B of FIG. 1 group X is an electron withdrawing group.

2. The preferred modifying agents of this invention are the cyclic imides of the dicarboxylic acids, saturated or unsaturated, cyclic or acyclic (FIG. 1, part A). In order to increase the electrophilicity and reactivity of the carbon atom in the carbonyl group of the dicarboxylic acid cyclic imide, the shared electron pair in the N—C bond of the cycle is shifted towards the nitrogen atom by introducing the electron withdrawing group in the X position (FIG. 1, part B).

N-Ethoxycarbonyl-phthalimide has been known for some time as a reagent for the N-phthaloylation of primary amino groups under mild conditions (Nefkins, G. H. L. et al., *Recl. Tray. Chim. Pays-Bas,* 79, 688, (1960); Worster, P. M., *J. Org. Chem.,* 45, 174-175 (1980)).

Figure 2:
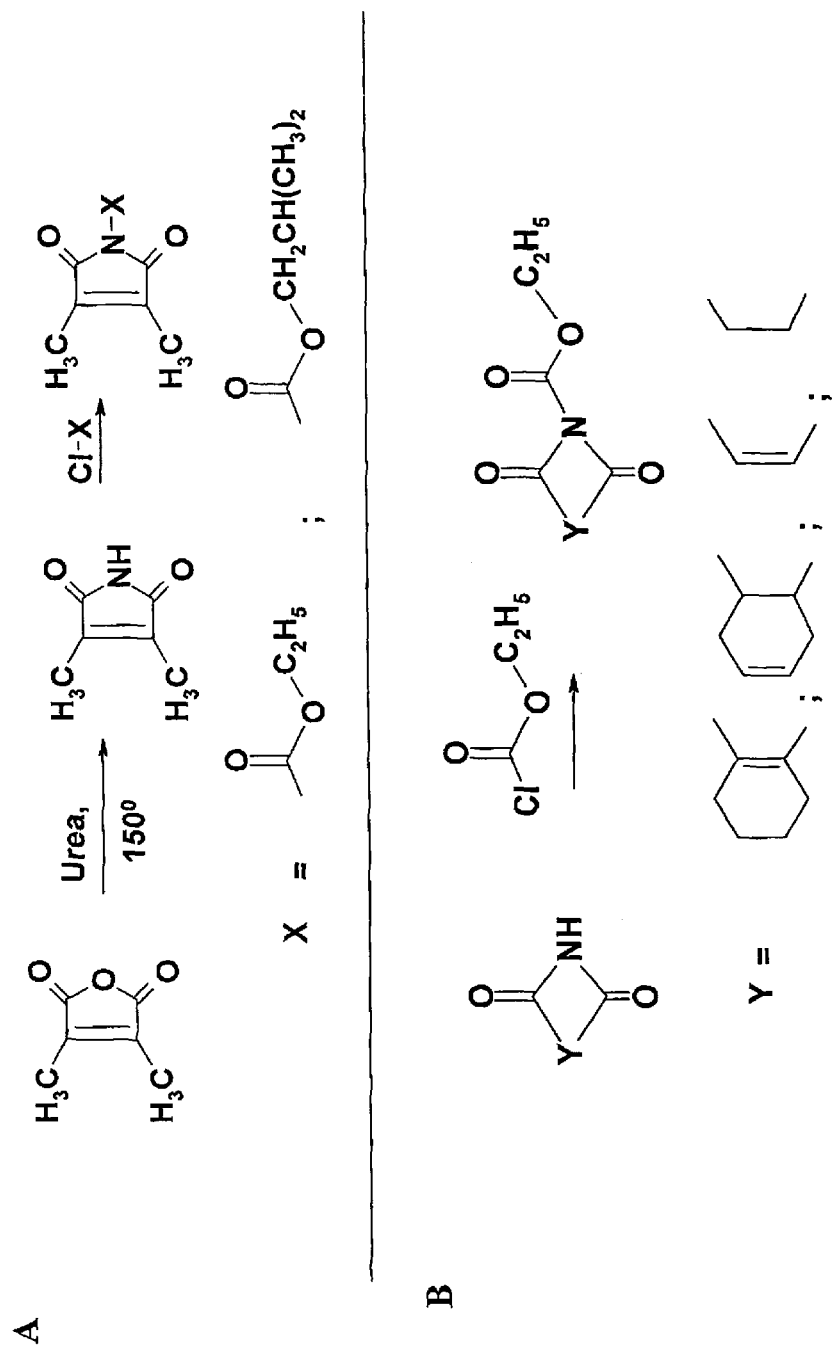
FIG. 2 parts A and B show synthesis schemes for modifying agent agents according to the present invention.

Commercially not-available reagents, dicarboxylic acid imides and N-alkoxycarbonylimides (FIG. 2), for reversible chemical modification were synthesized using methods described in A. Parker, A., *Synthetic Page,* 185, (2002). Detail experimental procedures for the synthesis of the novel modificators are presented in Example 1.

3. The preferred modification targets of this invention are protein amino groups, mostly the $\epsilon$-NH2 groups of lysine residues and also the $\alpha$-NH2 group of the first N-terminal amino acid. Modification via Lys residues is preferred for several reasons listed below:

a. Residues of this amino acid often play an important role in the enzymatic catalysis, the substrate recognition by enzymes or the enzyme structural conformation. Therefore, they often have detrimental effect on the enzyme activity.

b. Under the reaction conditions that are permissive and close to optimal for thermophilic polymerases (medium with pH 8-9), some of the Lys $\epsilon$-NH2 groups are not protonized. Therefore, those groups can act as nucleophiles attacking the carbon atom of the carbonyl groups of the dicarboxylic acid imides or anhydrides.

c. Strength of the bond between the modifying agent and the amino group directly depends on the pH value of ambient media, and it is inversely dependent on the reaction temperature. Therefore, the thermophilic enzyme may be deblocked and reactivated by elevating the temperature in Tris-containing buffers because the pH value of these buffers decreases with the increase of temperature.

4. The preferred modification media of this invention are solutions based either on water or on aprotic organic solvent (e.g. DMF, DMSO, dichlormethane, dimethylketone, ethylacetate, pyridine).

Figure 3:
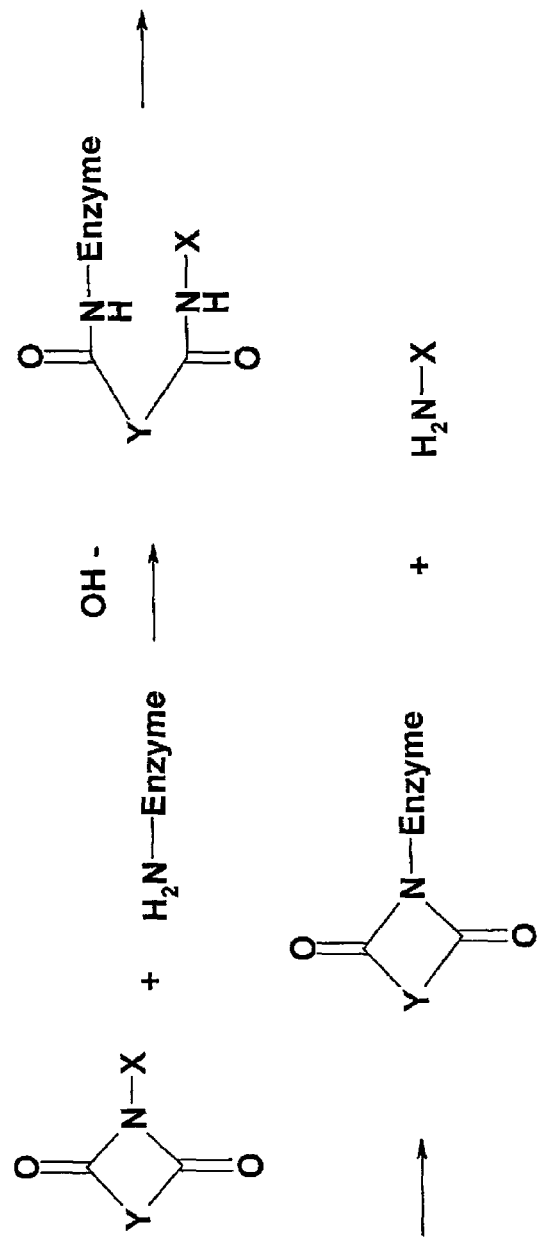
FIG. 3 shows a general schematic representation of the inactivation reaction of thermophilic enzymes with dicarboxylic acid imides as modifying agents.
Figure 4:
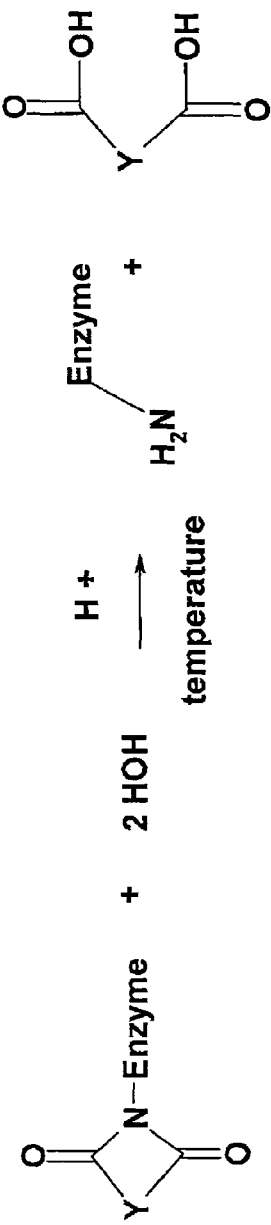
FIG. 4 shows a general schematic representation of the reactivation of an inactivated enzyme by deacylation.

The general schematic representation of the inactivation reaction of thermophilic enzymes with dicarboxylic acid imides as modifying agents is depicted in FIG. 3. The reactivation of the enzyme by deacylation, which is due to the temperature increase and the lower pH, is presented in FIG. 4.

1.2. The Reversible Chemical Modification of Taq DNA Polymerase

Figure 5:
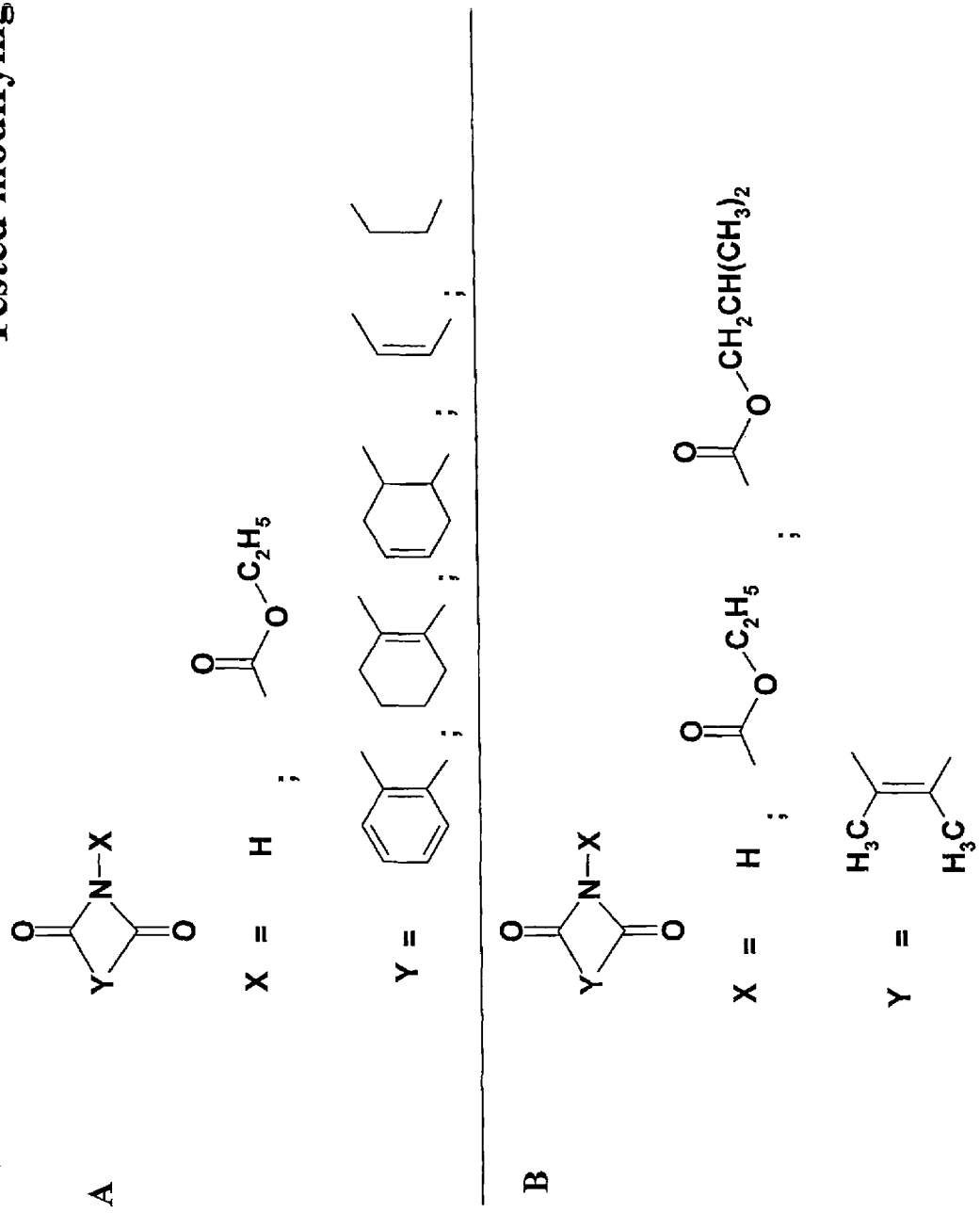
FIG. 5 parts A and B show various saturated and unsaturated, cyclic and acyclic dicarboxylic acid imides tested for their suitability to act as modifying reagents of Taq DNA polymerase.

Various saturated and unsaturated, cyclic and acyclic dicarboxylic acid imides differing by the carboxylic acid residues in the Y position (FIG. 5, part A) and by the electron acceptor groups in the X position (FIG. 5) were tested for their suitability to act as modifying reagents of Taq DNA polymerase. The enzyme was treated with different concentrations of the modifying reagents in different reaction media (aqueous or organic). Levels of the enzyme inactivation and subsequent reactivation were evaluated by comparison of the enzyme activity at 70° C. either without pre-incubation (reactivation) at 94° C. or after the enzyme reactivation at 94° C. The best results of these experiments are presented in Tables 1 and 2.

TABLE 1

Activity of Taq DNA polymerase modified with N-etoxycarbonyl-2,3-dimethylmaleinimide in aqueous solution, as measured by incorporation of [$H^3$]-dTTP into the polynucleotide adsorbed on DE-81 in 30 min at 70° C.

| Molar ratio of Taq DNA polymerase/N-etoxycarbonyl-2,3-dimethylmaleinimide | Activity at 70° C. (%) | |
|---|---|---|
| | Without preheating at 95° C. | After 10 min. preheating at 95° C. |
| 1/0 | 100 | ~100 |
| 1/40 | ~30 | ~100 |
| 1/80 | ~20 | ~90 |
| 1/110 | ~20 | ~100 |
| 1/160 | ~20 | ~90 |
| 1/320 | ~30 | ~90 |
| 1/640 | ~40 | ~50 |
| 1/1280 | ~90 | ~80 |

TABLE 2

Activity of Taq DNA polymerase treated with N-iso-butoxycarbonyl-2,3-dimethylmaleinimide in aqueous solution, as measured by incorporation of [$H^3$]-dTTP into the polynucleotide adsorbed on DE-81 in 30 min at 70° C.

| Molar ratio of Taq DNA polymerase/N-iso-butoxycarbonyl-2,3-dimethylmaleinimide | Activity at 70° C. (%) | |
|---|---|---|
| | Without preheating at 95° C. | After 10 min. preheating at 95° C. |
| 1/0 | 100 | ~100 |
| 1/40 | ~50 | ~90 |
| 1/80 | ~40 | ~100 |
| 1/160 | ~30 | ~80 |
| 1/320 | ~10 | ~40 |

Analysis of the data obtained with different modifying reagents indicates the following preferred embodiments of the invention:

1. Modifying agent: N-ethoxycarbonyl-2,3-dimethylmaleinimide.
2. Modification medium: aqueous solution.
3. Molar ratio of Taq DNA polymerase/modifying agent (aqueous solution): 1/110.

Figure 6:
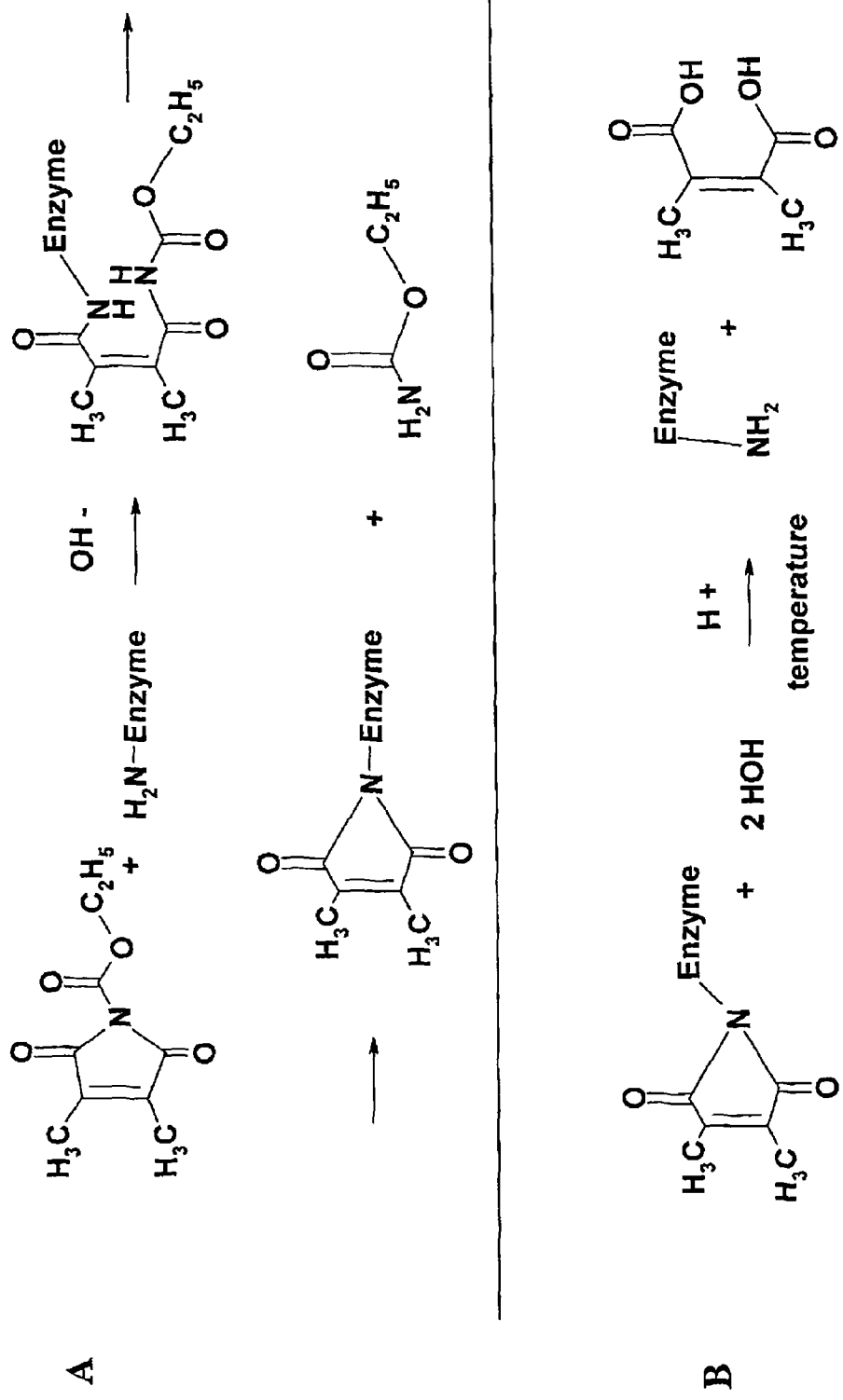
FIG. 6 parts A and B show enzyme inactivation and reactivation schemes, respectively.

Enzyme inactivation and reactivation scheme is presented in FIG. 6, parts A and B, respectively. Several independent experiments showed that the modified Taq DNA polymerase retained 21±6% of specific activity at 70° C. temperature without preheating, while incubation for 10 min at 94° C. temperature resulted almost in the complete restoration of the enzyme activity.

1.3. The Reversible Chemical Modification of Pfu DNA Polymerase

Chemical modification of the other thermophilic DNA polymerase, Pfu, using imides of dicarboxylic acids also yielded reversibly inactivated enzyme (Table 3). This modified DNA polymerase was reactivated by incubation at 95° C. The enzyme activity was measured both at 72° C. and at 50° C.

TABLE 3

Activity of Pfu DNA polymerase modified with N-etoxycarbonyl-2,3-dimethylmaleinimide in aqueous solution, as measured by incorporation of [$H^3$]-dTTP into the polynucleotide adsorbed on DE-81 in 30 min.

| Molar ratio of the Pfu/N-etoxycarbonyl-2,3-dimethylmaleinimide | Activity at 50° C. (%) | | Activity at 72° C. (%) | |
|---|---|---|---|---|
| | Without preheating at 95° C. | After 10 min. preheating at 95° C. | Without preheating at 95° C. | After 10 min. preheating at 95° C. |
| 1/0 | 100 | ~100 | 100 | ~100 |
| 1/200 | ~20 | ~100 | ~90 | ~100 |
| 1/800 | ~0 | ~100 | ~60 | ~90 |

2. Properties of Taq DNA Polymerase Modified with N-Ethoxycarbonyl-2,3-Dimethylmaleinimide

2.1. Temperature Effect on Activity of the Modified Taq DNA Polymerase

Figure 7:
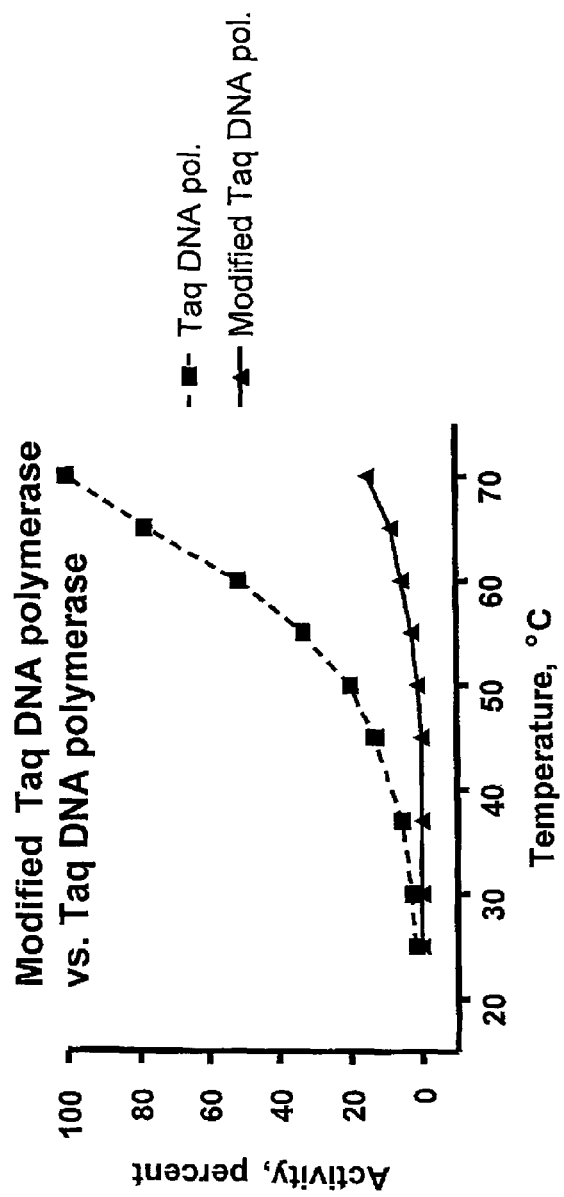
FIG. 7 shows a graph comparing the activity of Taq DNA polymerase modified according to the present invention with the activity of unmodified Taq DNA polymerase, at different temperatures.

Activity of the modified DNA polymerase was compared with the activity of the unmodified enzyme at different temperatures (FIG. 7). Experimental data indicate that modified Taq DNA polymerase was practically inactive up to 50° C. The incubation at 94° C. was required to reactivate the enzyme. Residual ~20% activity of the modified DNA polymerase was observed at 70° C. temperature, which could be attributed to partial deblocking and reactivation of the enzyme. Thus, the modified enzyme is suitable for use in experiments where residual activity of Taq DNA polymerase is undesirable, like during assembly of PCR mixture and the initial annealing of primers. Reduced enzyme activity during these steps is crucial in avoiding the formation of primer dimers and the appearance of unspecific PCR byproducts.

2.2. Reactivation of the Modified Taq DNA Polymerase

Reactivation experiments performed at different temperatures (FIG. 8) indicated that the modified DNA polymerase of this invention regained full activity, while being preheated at 90° C. for several minutes. Studies of the kinetics of the reactivation process at 95° C. indicated that the modified enzyme regained ~60% and ~90% activity after the incubation for 0.5 minute and 1 minute, respectively (Table 4). This fast and efficient reactivation of the modified enzyme of the invention is an obvious advantage.

TABLE 4

Reactivation kinetics of the modified Taq DNA polymerase at 95° C.

| Incubation time at 95° C. (min.) | Activity at 50° C. (%) |
|---|---|
| 0 | ~0 |
| 0.5 | ~60 |
| 1 | ~90 |
| 1.5 | ~90 |
| 2.0 | ~100 |
| 3.0 | ~100 |

Figure 8:
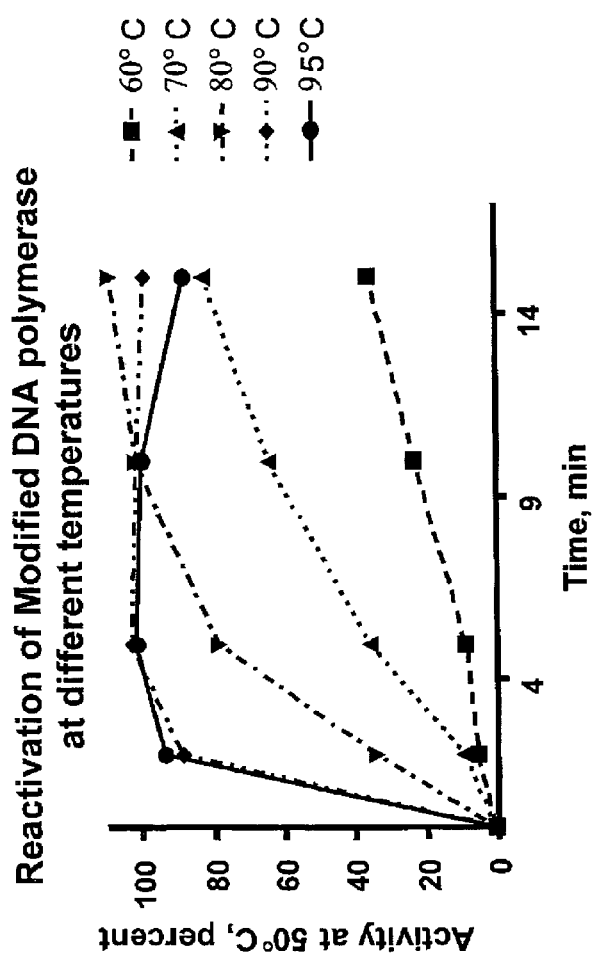
FIG. 8 shows a graph comparing the reactivation of Taq DNA polymerase modified according to the present invention at different temperatures.

Data presented in FIG. 8 and Table 3 demonstrate that the Taq DNA polymerase modified with N-ethoxycarbonyl-2,3-dimethylmaleinimide was efficiently reactivated at temperatures and time intervals used in the initial steps of conventional PCR reaction.

2.3. Effect of pH and $Mg^{2+}$ on Activity of the Modified Taq DNA Polymerase The modified DNA polymerase exhibited ≥80% activity within the pH 8.3-8.7 range (Table 5). The enzyme demonstrated ≥70% activity within the 1.5-5.0 mM range of $Mg^{2+}$ concentrations (Table 6).

TABLE 5

Activity of Taq DNA polymerase modified with N-etoxycarbonyl-2,3-dimethylmaleinimide at different pH, as measured by incorporation of $[H^3]$-dTTP into the PCR product

| Ambient pH | Activity at 70° C. (%) |
|---|---|
| 8.2 | ~30 |
| 8.3 | ~80 |
| 8.4 | ~100 |
| 8.5 | ~100 |

TABLE 5-continued

Activity of Taq DNA polymerase modified with N-etoxycarbonyl-2,3-dimethylmaleinimide at different pH, as measured by incorporation of $[H^3]$-dTTP into the PCR product

| Ambient pH | Activity at 70° C. (%) |
|---|---|
| 8.6 | ~100 |
| 8.7 | ~100 |
| 8.8 | ~60 |

TABLE 6

Activity of Taq DNA polymerase modified with N-etoxycarbonyl-2,3-dimethylmaleinimide at different $Mg^{2+}$ concentrations, as measured by incorporation of $[H^3]$-dTTP into the PCR product.

| $[Mg^{2+}]$, (mM) | Activity at 70° C. (%) |
|---|---|
| 1 | ~0 |
| 1.5 | ~70 |
| 2.0 | ~70 |
| 2.5 | ~100 |
| 3.0 | ~100 |
| 3.5 | ~100 |
| 4.0 | ~90 |
| 5.0 | ~70 |
| 6.0 | ~30 |
| 7.0 | ~20 |
| 8.0 | ~10 |

Data presented in table 5 show that the Taq DNA polymerase modified with N-ethoxycarbonyl-2,3-dimethylmaleinimide retains its activity within a wide range of $Mg^{2+}$ concentrations.

2.4. Inactivation of the 5'-3' Exonuclease Activity of Taq DNA Polymerase

Figure 9:
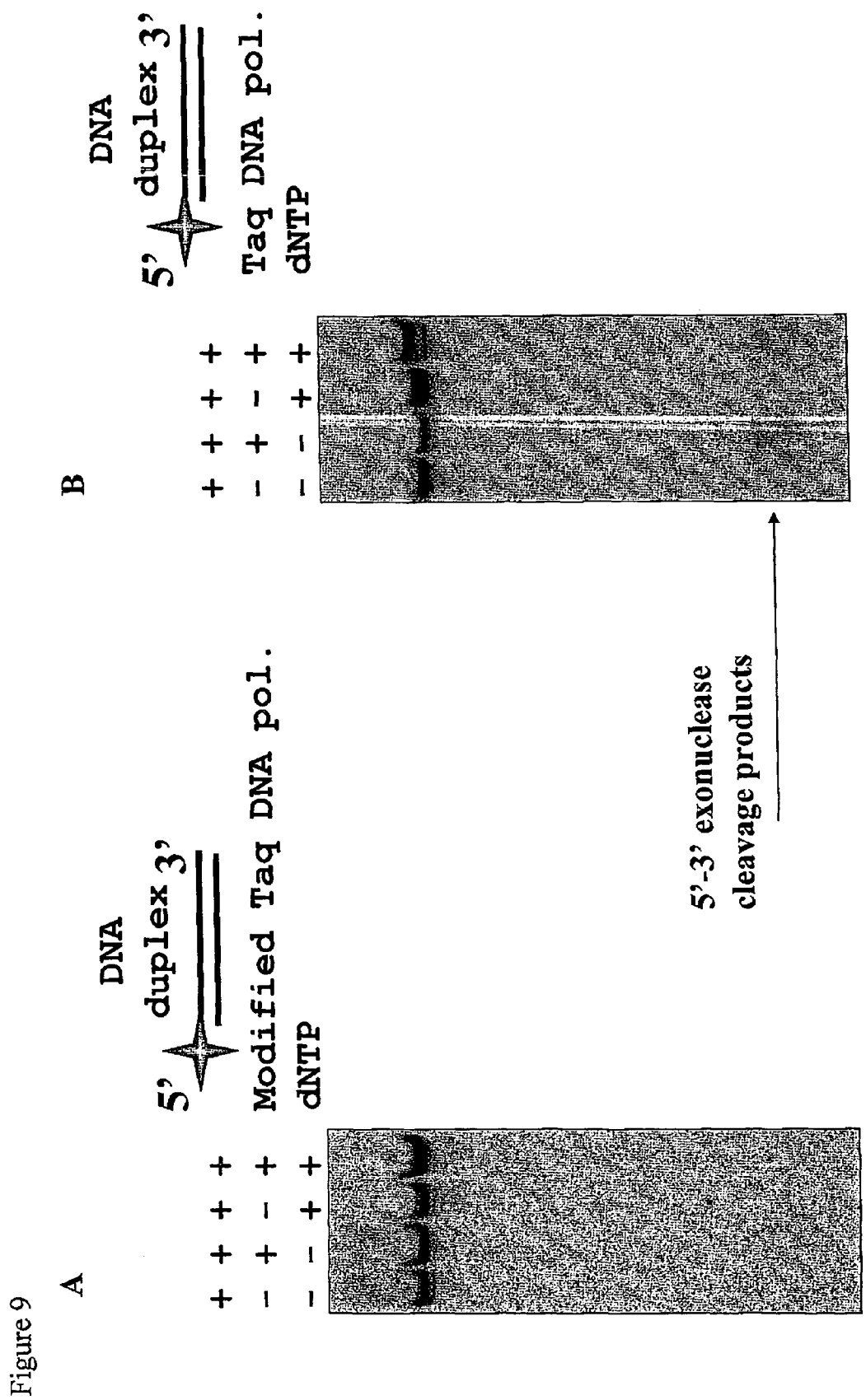
FIG. 9 parts A and B show gel photographs which represent the results of Example 10 in which the 5' to 3' exonuclease activity of the modified Taq DNA polymerase was compared with the activity of the unmodified enzyme at 37° C.

The 5'-3' exonuclease activity of the modified Taq DNA polymerase was compared with the activity of the unmodified enzyme at 37° C. To monitor the exonuclease activity of both versions of Taq DNA polymerase, we measured cleavage of the 5'-labelled oligonucleotide duplexes (see example 10). Positive control experiment with the intact Taq DNA polymerase (FIG. 9, part A) indicated the presence of a strong exonuclease activity both in the presence and the absence of dNTPs. The chemical modification of Taq DNA polymerase produced an enzyme practically devoid of exonuclease activity (FIG. 9, part B). This feature of the modified Taq DNA polymerase may have some practical implications because of the reduced 5'-3' degradation of the non-specific annealed primers.

3. Features of the Taq DNA Polymerase Modified with N-Ethoxycarbonyl-2,3-Dimethylmaleinimide

3.1. Specificity and Efficiency of the Modified DNA Polymerase

Figure 10:
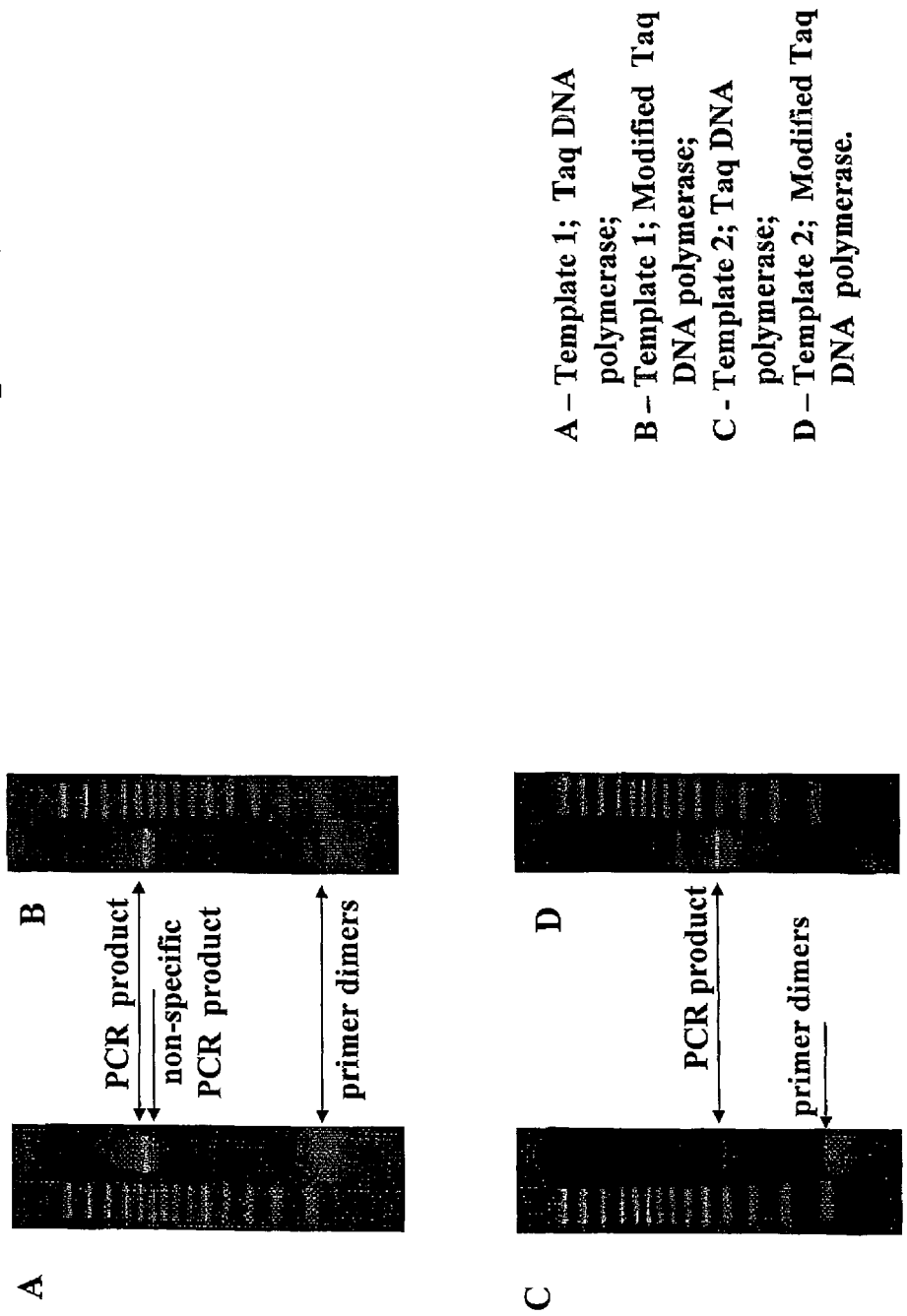
FIG. 10 parts A to D show gel photographs illustrating the results of an experiment to compare the specificity and efficiency of the modified Taq DNA polymerase with Taq DNA polymerase after PCR with two different templates.

PCR mixtures were set up at room temperature with either the modified DNA polymerase or with the unmodified one (FIG. 10). Two sets of PCR primers were used to amplify fragments of either the CFTR gene or the insulin gene, using human genome DNA as template. A lesser yield of unspecific PCR byproducts was observed with the modified DNA polymerase in both cases (FIG. 10). The use of the modified DNA polymerase also resulted in the higher yield of the insulin amplicon, while the yield of the byproducts caused by the primer dimerization was lower under these conditions (FIG. 9, part C-D).

Figure 11:
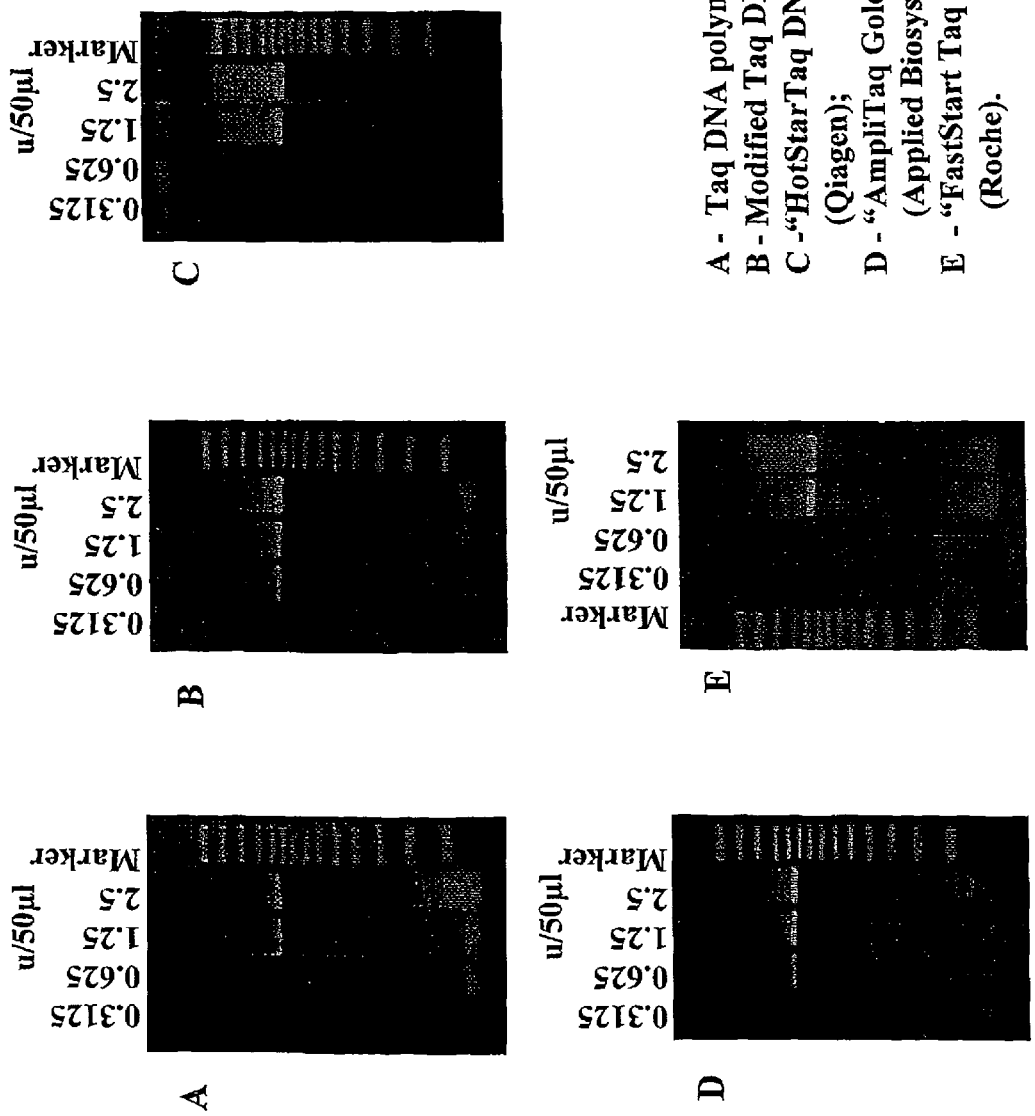
FIG. 11 parts A to E show gel photographs illustrating the results of an experiment to compare the effect of en me concentration on the PCR sensitivity with different Taq DNA polymerase enzymes.

3.2. Comparison of the Modified DNA Polymerase of the Invention with Commercial Taq DNA Polymerases Specifically Designed for the Hot-Start PCR PCR efficiency with the modified DNA polymerase was compared with that of chemically modified DNA polymerases from leading vendors: Qiagen (HotStarTaq DNA polymerase), Applied Biosystems (AmpliTaq Gold DNA polymerase) and Roche (FastStart Taq DNA polymerase). The following features of the enzymes were compared:

Effect of the enzyme concentration on the PCR sensitivity (FIG. 11).

Figure 12:
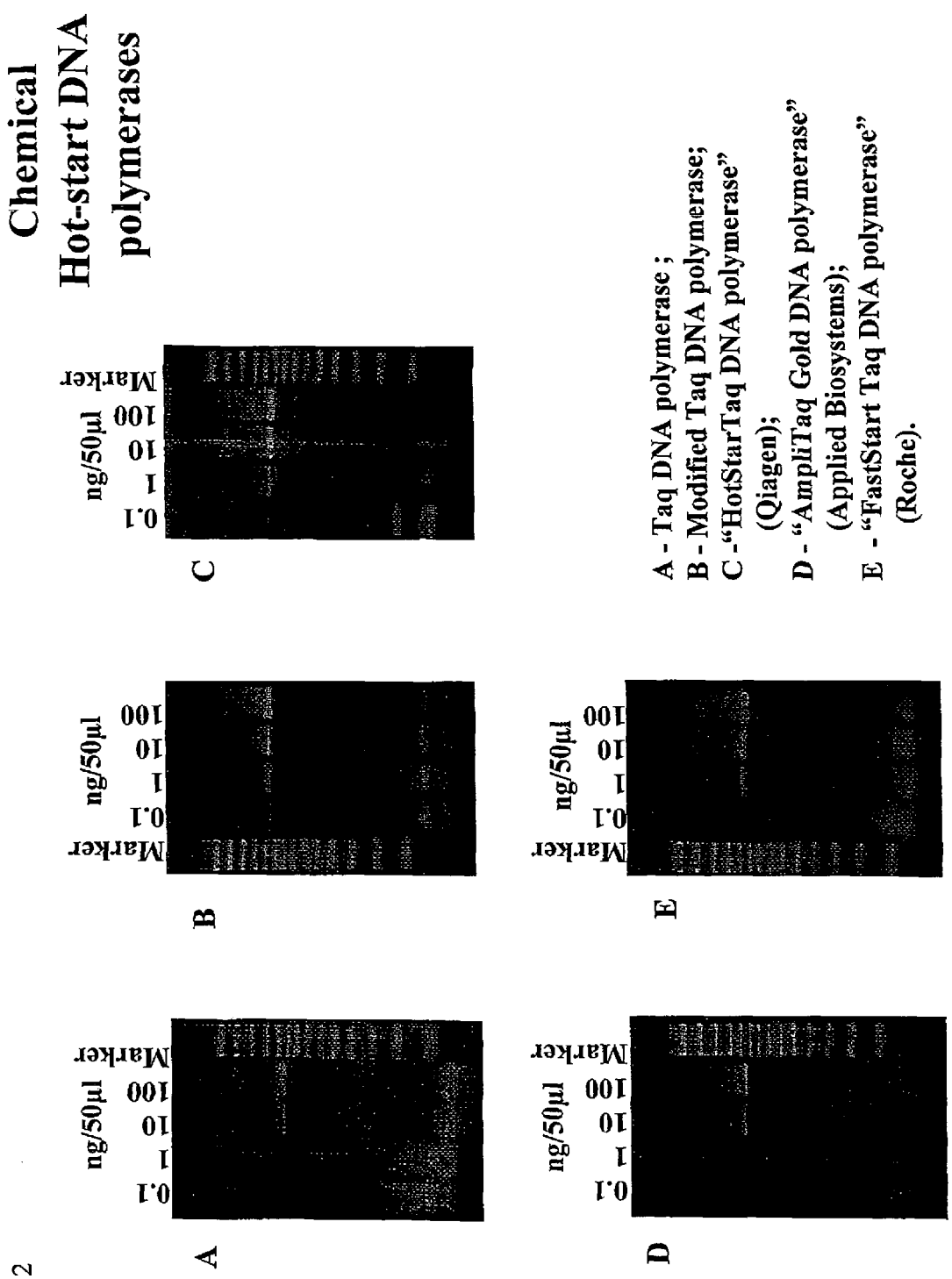
FIG. 12 parts A to E show gel photographs illustrating the results of an experiment to compare the effect of target DNA concentration on the PCR sensitivity with different Taq DNA polymerase enzymes.

Effect of the target DNA concentration on the PCR sensitivity (FIG. 12).

Figure 13:
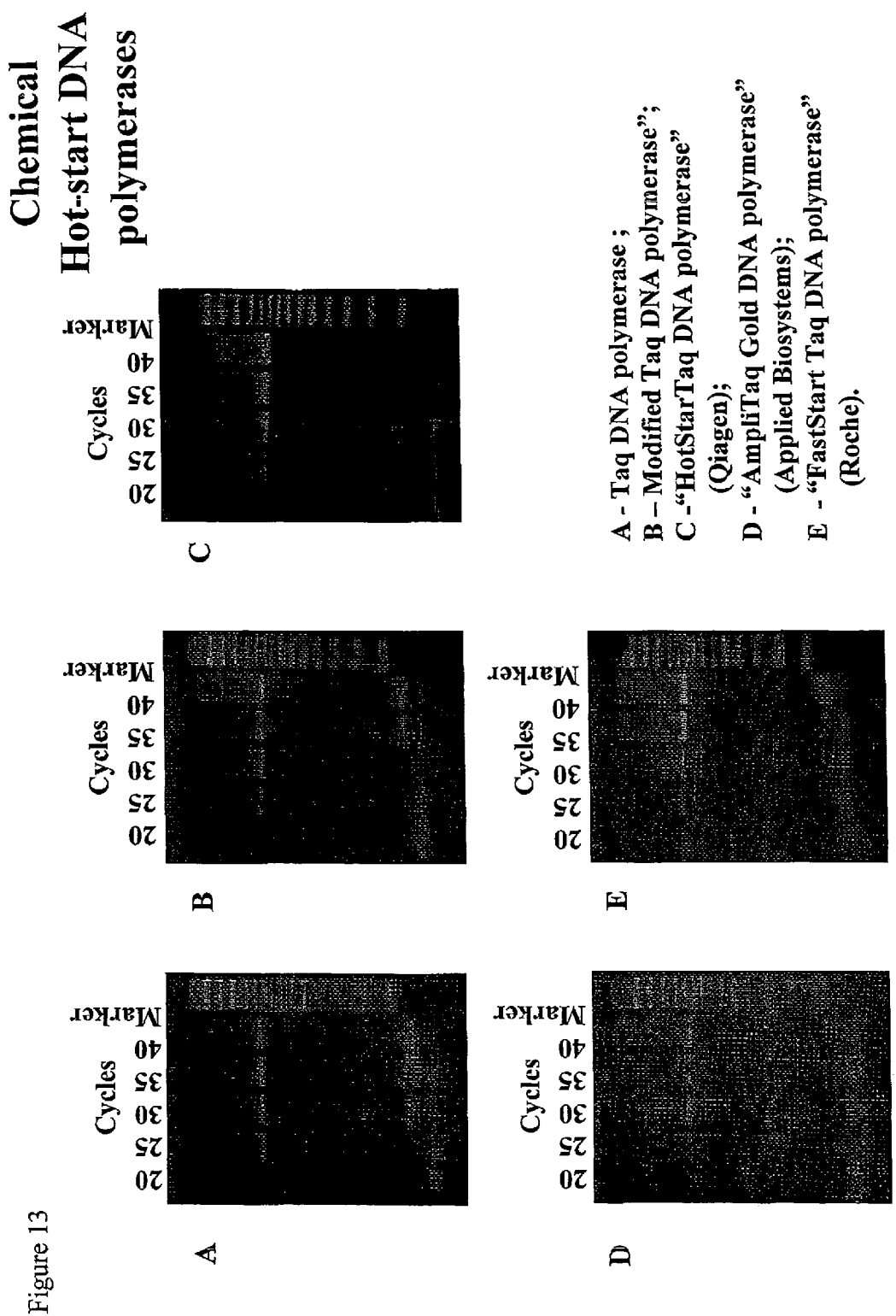
FIG. 13 parts A to E show gel photographs illustrating the results of an experiment to compare the effect of the number of cycles on the PCR sensitivity with different Taq DNA polymerase enzymes.

Effect of the number of cycles on the PCR sensitivity (FIG. 13).

Figure 14:
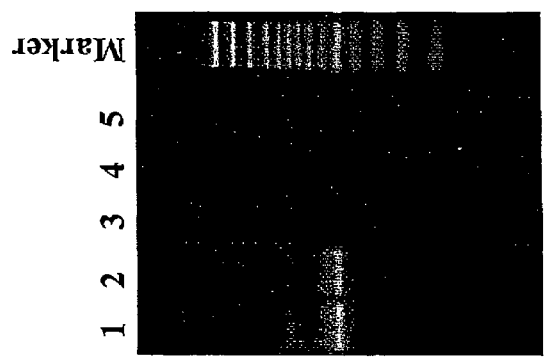
FIG. 14 shows a gel photograph illustrating the results of an experiment to compare the performance of different Taq DNA polymerase enzymes in the "Fast PCR" application.

Performance in the "Fast PCR" application (FIG. 14).

Figure 15:
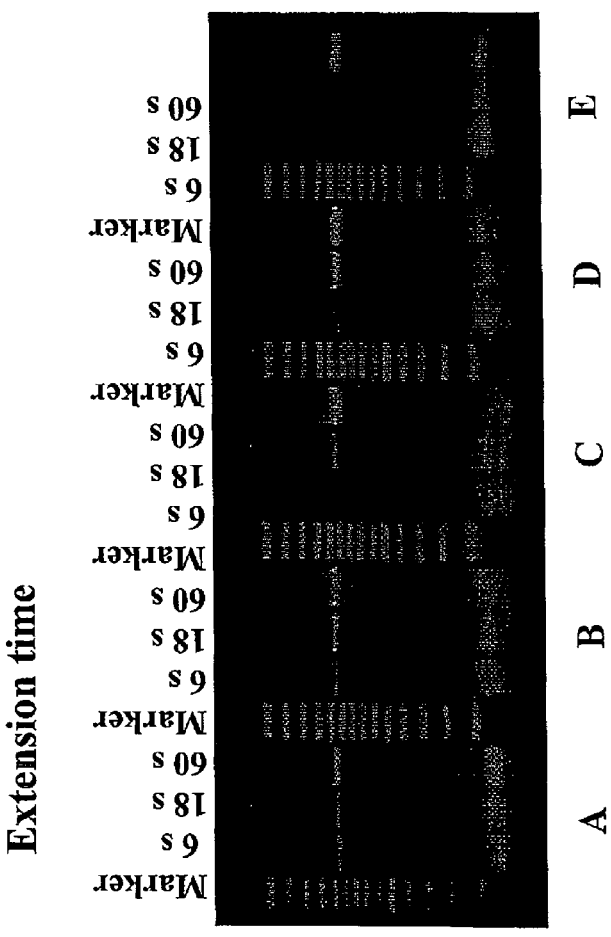
FIG. 15 shows a gel photograph illustrating the results of an experiment to compare the rate of DNA polymerization and primer extension with different Taq DNA polymerase enzymes.

Rate of DNA polymerization and primer extension (FIG. 15).

The PCR experiments demonstrated higher sensitivity for the modified DNA polymerase regarding both the enzyme concentration and the target DNA concentration, as compared with the DNA polymerases from other vendors. Also, the primer extension time with the modified DNA polymerase of the invention was shorter and it exhibited superior performance in the "Fast PCR" application.

EXAMPLES

Example 1

Synthesis of Putative Modificators 2,3-dimethylmaleimide

A mixture of 2,3-dimethylameic anhydride (2.5 g, 20 mmol), urea (1.2 g, 20 mmol) and sodium chloride (4.05 g, 70 mmol) was transferred to a flask fitted with an air condenser and was heated with stirring at 150° C. until the organic components were seen to fuse. Heating was continued for 30 min. Boiling water (10 ml) was then added. The cooled mixture was diluted with water (15 ml) and extracted (ethyl acetate, 4×30 ml). The combined organic layers were washed (sat.aq. NaCl, 20 ml), dried ($Na_2SO_4$) and concentrated in vacuum. The residue was crystallised from ethyl alcohol. Purification in chloroform and hexane on a silica gel column gave 2,3-dimethylmaleimide as a colourless crystalline solid (yield 79%).

$^1$H NMR ($CDCl_3$) δ 1.99 (6H, s, 2×$CH_3$).

N-Ethoxycarbonyl-2,3-dimethylmaleimide

Ethyl chloroformate (1.5 ml, 15.6 mmol) was added dropwise to a stirred solution of 2,3-dimethylmaleimide (1.5 g, 12 mmol) and triethylamine (2 ml, 14 mmol) in dimethylformamide (10 ml) at 0-5° C. The reaction mixture was allowed to warm to room temperature and stand for 4 h. Methyl alcohol (10 ml) was added, diluted with chloroform (50 ml) and washed with water (3×20 ml). The chloroform solution was dried ($Na_2SO_4$) and concentrated in vacuum to give N-ethoxycarbonyl-2,3-dimethylmaleimide (yield 80%).

$^1$H NMR ($CDCl_3$) δ 1.42 (3H, t, $OCH_2CH_3$), 2.04 (6H, s, 2×$CH_3$), 4.43 (2H, q, $CH_2$).

N-iso-Butoxycarbonyl-2,3-dimethylmaleimide iso-Butyl chloroformate (0.13 ml, 1 mmol) was added dropwise to a stirred solution of 2,3-dimethylmaleimide (0.1 g, 0.8 mmol) and triethylamine (0.13 ml, 0.92 mmol) in dimethylformamide (1.5 ml) at 0-5° C. The reaction mixture was allowed to warm to room temperature and stand for 4 h. Methyl alcohol (0.5 ml) was added, diluted with chloroform (5 ml) and washed with water (3×3 ml). The chloroform solution was dried ($Na_2SO_4$) and concentrated in vacuum to give N-iso-butoxycarbonyl-2,3-dimethylmaleimide (yield 83%).

$^1$H NMR ($CDCl_3$) δ 1.04 (6H, d, 2×$CH_3$), 1.28 (1H, s, CH), 2.05 (6H, s, 2×$CH_3$), 4.15 (2H, d, $CH_2$).

N-Ethoxycarbonyl-3,4,5,6-tetrahydrophthalimide

Ethyl chloroformate (0.38 ml, 4.3 mmol) was added dropwise to a stirred solution of 3,4,5,6-tetrahydrophthalimide (0.5 g, 3.3 mmol) and triethylamine (0.53 ml, 3.8 mmol) in dimethylformamide (6 ml) at 0-5° C. The reaction mixture was allowed to warm to room temperature and stand for 4 h. Methyl alcohol (3 ml) was added, diluted with chloroform (50 ml) and washed with water (3×150 ml). The chloroform solution was dried ($Na_2SO_4$) and concentrated in vacuum to give N-ethoxycarbonyl-3,4,5,6-tetrahydrophthalimide (yield 42%).

$^1$H NMR ($CDCl_3$) δ 1.36 (3H, t, $CH_3$), 1.75 (4H, m, $CH_2$), 2.37 (4H, m, $CH_2$), 4.37 (2H, q, $CH_2$).

N-Ethoxycarbonyl-1,2,3,6-tetrahydrophthalimide

Ethyl chloroformate (0.18 ml, 1.89 mmol) was added dropwise to a stirred solution of 1,2,3,6-tetrahydrophthalimide (0.22 g, 1.45 mmol) and triethylamine (0.23 ml, 1.67 mmol) in dimethylformamide (2 ml) at 0-5° C. The reaction mixture was allowed to warm to room temperature and stand for 4 h. Methyl alcohol (1 ml) was added, diluted with chloroform (20 ml) and washed with water (3×10 ml). The chloroform solution was dried ($Na_2SO_4$) and concentrated in vacuum to give N-ethoxycarbonyl-1,2,3,6-tetrahydrophthalimide (yield 82%).

$^1$H NMR ($CDCl_3$) δ 1.4 (3H, t, $CH_3$), 2.3 (2H, m, $CH_2$), 2.65 (2H, m, $CH_2$), 3.2 (2H, m, CH), 5.95 (2H, m, CH=).

N-Ethoxycarbonyl-maleimide

Ethyl chloroformate (0.38 ml, 4 mmol) was added dropwise to a stirred solution maleimide (0.3 g, 3 mmol) and triethylamine (0.5 ml, 3.5 mmol) in dimethylformamide (2 ml) at 0-5° C. The reaction mixture was allowed to warm to room temperature and stand for 4 h. Methyl alcohol (1 ml) was added, diluted with chloroform (20 ml) and washed with water (3×10 ml). The chloroform solution was dried ($Na_2SO_4$) and concentrated in vacuum. The residue was purified in chloroform and hexane on a silica gel column to give N-ethoxycarbonyl-maleimide (yield 41%).

$^1$H NMR ($CDCl_3$) δ 1.34 (3H, t, $CH_3$), 4.27 (2H, q, $CH_2$), 6.21 (1H, d, CH=), 6.72 (1H, d, CH=).

N-Ethoxycarbonyl-succinimide

Ethyl chloroformate (1.24 ml, 13.1 mmol) was added dropwise to a stirred solution of succinimide (1.0 g, 10 mmol) and triethylamine (1.6 ml, 11.5 mmol) in dimethylformamide (10 ml) at 0-5° C. The reaction mixture was allowed to warm to room temperature and stand for 3 h. Methyl alcohol (1 ml) was added, diluted with chloroform (40 ml) and washed with water (2×20 ml). The chloroform solution was dried ($Na_2SO_4$) and concentrated in vacuum to give N-ethoxycarbonyl-succinimide (yield 60%).

¹H NMR (CDCl₃) δ 1.42 (3H, t, CH₃), 2.84 (4H, m, CH₂), 4.46 (2H, q, CH₂).

All chemicals for the synthesis of putative modificators were purchased from commercial suppliers. $^1$H NMR spectra were recorded on a Varian Inova 300 using residual solvent signal as reference.

Example 2

Polymerase Activity Assays

The measure of the enzyme activity was incorporation of [$^3$H]-dTTP into polynucleotide fraction. One unit of polymerase activity is defined as the enzyme amount which incorporates 10 nmoles of deoxyribonucleotides into the polynucleotide adsorbed on DE-81 in 30 min at 70° C.

For activity assays, Taq DNA polymerase was diluted up to 4 u/ml with the dilution buffer of the following composition: 20 mM Tris-HCl (pH 8.8 at 25° C.), 1 mM EDTA, 1 mM DTT, and BSA (0.1 mg/ml). Reactions were carried out at 70° C. for 30 min with 5 µl of the diluted enzyme in 50 µl of the reaction buffer of the following composition: 67 mM Tris-HCl (pH 8.8 at 25° C.), 50 mM NaCl, 6.7 mM MgCl₂, 1 mM DTT, and BSA (0.1 mg/ml). The reaction buffer was supplemented with 0.2 mM dNTP, [3H]-dTTP (0.4 MBq/ml) and 0.75 mM activated DNA from calf thymus.

Activity of the modified enzymes was measured either with the pre-incubation step, or without it, for 10 min at 95° C. in the pre-heating buffer of the following composition: 20 mM Tris-HCl (pH 8.25 at 25° C.), 100 mM KCl, 2 mM MgCl₂, 0.5% Tween 20, 0.5% Nonidet P40, and 16% glycerol.

Example 3

Modification of Taq DNA Polymerase with N-Ethoxycarbonyl-2,3-Dimethylmaleinimide Recombinant Taq DNA polymerase was used at initial concentration of 10.8 mg/ml (800000 u/ml; ~0.12 mM). An aliquot (80 µl) of the enzyme solution was dialyzed against 1000-fold volume of the dialysis buffer [100 mM H₃BO₃—NaOH (pH 8.5 at 25° C.)] for 24 hours at 4° C. About 350 µl of the enzyme solution were recovered after dialysis. The enzyme concentration was close to 0.037 mM.

A set of N-ethoxycarbonyl-2,3-dimethylmaleinimide solutions (736 mM, 368 mM, 184 mM, 92 mM, 63.25 mM, 46 mM and 23 mM) was prepared by serial dilutions of the 184 mM stock in N,N dimethylformamide (DMF).

Aliquots (35 µl) of the enzyme solution were mixed with 2.25 µl aliquots of the N-ethoxycarbonyl-2,3-dimethylmaleinimide solutions described above resulting in the following molar ratios of Taq DNA polymerase to N-ethoxycarbonyl-2,3-dimethylmaleinimide: 1/1280 1/640, 1/320, 1/160, 1/110, 1/80, 1/40. The mixtures were incubated for 20 hours at 4° C. to modify the Taq DNA polymerase. Control samples, in which the enzyme was left unmodified (e.g., the ratio was 1/0), were obtained by mixing the Taq DNA polymerase with a 2.25 µl aliquot of DMF. These control samples were incubated under the same conditions as the modified ones.

The samples of the unmodified Taq DNA polymerase and the modified Taq DNA polymerases were diluted 250-fold in the pre-heating buffer (see Example 2) and activities of the modified enzyme were measured both before heat-reactivation and after it, as described in the Example 2. Activities of both inactivated and heat-reactivated DNA polymerases were determined as described in the Example 2, and the data were normalized to activity of the unmodified Taq DNA polymerase Example 4

Modification of Taq DNA Polymerase with N-Isobutoxycarbonyl-2,3-Dimethylmaleinimide Recombinant Taq DNA polymerase was used at initial concentration of 10.8 mg/ml (800000 u/ml; ~0.12 mM). An aliquot (110 µl) of the enzyme solution was dialyzed against 1000-fold volume of the dialysis buffer [100 mM H₃BO₃—NaOH (pH 8.5 at 25° C.)] for 24 hours at 4° C. About 350 µl of the enzyme solution were recovered after dialysis. The enzyme concentration was close to 0.037 mM.

A set of isobutoxycarbonyl-2,3-dimethylmaleinimide solutions (250 mM, 125 mM, 62.5 mM and 31.25 mM) was prepared by serial dilutions of the 250 mM stock in N,N dimethylformamide (DMF).

Aliquots (20.6 µl) of the diluted enzyme solution were mixed with 1 µl of N-isobutoxycarbonyl-2,3-dimethylmaleinimide solutions described above resulting in different molar ratios of Taq DNA polymerase to N-isobutoxycarbonyl-2,3-dimethylmaleinimide (1/320, 1/160, 1/80 and 1/40). The mixtures were incubated 20 hours at 4° C. to modify the Taq DNA polymerase. Control samples, in which the enzyme was left unmodified (e.g., the ratio was 1/0), were obtained by mixing the Taq DNA polymerase with a 1 µl aliquot of DMF. These control samples were incubated under the same conditions as the modified ones. The heat-reactivation of the modified enzymes was performed as described in the Example 3.

Example 5

Modification of Pfu DNA Polymerase with N-Ethoxycarbonyl-2,3-Dimethylmaleinimide Native Pfu DNA polymerase was used at initial concentration of 1.065 mg/ml (24000 u/ml; ~0.0118 mM). An aliquot (40 µl) of the enzyme solution was dialyzed against 5000-fold volume of the dialysis buffer [100 mM H₃BO₃—NaOH (pH 8.5 at 25° C.)] for 24 hours at 4° C. About 130 µl of the enzyme solution were recovered after dialysis. The enzyme concentration was close to 0.0036 mM.

A set of N-ethoxycarbonyl-2,3-dimethylmaleinimide solutions (72 mM, 18 mM) was prepared by serial dilutions of the 720 mM stock in N,N dimethylformamide (DMF). Aliquots (25 µl) of the enzyme solution were mixed with 1 µl aliquots of the N-ethoxycarbonyl-2,3-dimethylmaleinimide solutions described above resulting in the following molar ratios of Pfu DNA polymerase to N-ethoxycarbonyl-2,3-dimethylmaleinimide: 1/800, 1/200. The mixtures were incubated for 20 hours at 4° C. to modify the Pfu DNA polymerase. Control samples, in which the enzyme was left unmodified (e.g., the ratio was 1/0), were obtained by mixing the Pfu DNA polymerase with a 1 µl aliquot of DMF. These control samples were incubated under the same conditions as the modified ones.

The samples of the unmodified Pfu DNA polymerase and the modified Pfu DNA polymerases were diluted in the pre-heating buffer (see Example 2) either 9-fold for measurements at 50° C., or 24-fold for measurements at 72° C. (see Example 2). Activities of the modified enzymes were measured either with the pre-incubation step, or without it, for 10 min at 95° C.

For activity assays, Pfu DNA polymerase was diluted up to 11 u/ml (91 u/ml for measurements at 50° C.) in the dilution buffer (see Example 2). Reactions were carried out either at 50° C., or at 72° C. for 30 min. Aliquots (5 µl) of the diluted enzyme were added to 50 µl of the reaction buffer of the following composition: 20 mM Tris-HCl (pH 8.8 at 25° C.), 10 mM $(NH_4)_2SO_4$, 10 mM KCl, 2 mM $MgCl_2$, 0.1% Triton X-100, and BSA (0.1 mg/ml) supplemented with, 0.2 mM dNTP, [3H]-dTTP (0.4 MBq/ml) and 0.75 mM activated DNA from calf thymus.

Example 6

Effect of Temperature on Activities of the Taq DNA Polymerase Modified with N-Ethoxycarbonyl-2,3-Dimethylmaleinimide and the Unmodified Taq DNA Polymerase The activity assay for both DNA polymerases was as described in the Example 2 with the following modifications:
1. DNA polymerization using the unmodified DNA polymerase was carried out in the buffer of the following composition: 10 mM Tris-HCl (pH 8.8 at 25° C.), 50 mM KCl, 1.5 mM $MgCl_2$, and 0.08% Nonidet P40.
2. DNA polymerization using the modified DNA polymerase was carried out in the buffer of the following composition: 20 mM Tris-HCl (pH 8.3 at 25° C.), 20 mM KCl, 5 mM $(NH_4)_2SO_4$, and 1.5 mM MgCl2.

Enzyme activities at different temperatures were normalized to the activity of the unmodified Taq DNA polymerase at 70° C.

Example 7

Temperature Effect on Reactivation of the Taq DNA Polymerase Modified with N-Ethoxycarbonyl-2,3-Dimethylmaleinimide The activity of modified Taq DNA polymerase was assayed as described in the Example 2. The enzyme was pre-incubated at different temperatures in the pre-heating buffer (see Example 2), its activity was measured at 50° C. in the reaction buffer of the following composition: 50 mM Tris (pH 8.4 at 25° C.), 10 mM KCl, 5 mM $(NH_4)_2SO_4$ and 2 mM $MgCl_2$. The activity of the modified DNA polymerase was normalized the activity of the unmodified one.

Example 8

Effect of Ambient pH on Activity of Taq DNA Polymerase Modified with N-Ethoxycarbonyl-2,3-Dimethylmaleinimide Activity of Taq DNA polymerase modified with N-ethoxycarbonyl-N-2,3-dimethylmaleinimide at different pH during was measured by incorporation [$^3$H]-dTTP nucleotide into the PCR product.

Sets of PCR were carried out at the following pH values determined at 25° C.: 8.2, 8.3, 8.4, 8.5, 8.6, 8.7, and 8.8. The reactions were preformed in the GeneAmp® PCR System 9700 (Applied Biosystems) using 1.25 units of the modified enzymes in aliquots (500 of the reaction buffer of the following composition: 20 mM Tris-HCl (pH values indicated above), 20 mM KCl, 5 mM $(NH_4)_2SO_4$, 1.5 mM $MgCl_2$ supplemented with 0.2 mM dNTP, 0.8 MBq/ml [$^3$H]-dTTP, 0.5 1.1M of both PCR primers ([SEQ ID NO: 1] 5'-GCTG-CATCATATAAGTTGCC-3' and [SEQ ID NO: 2] 5'-AAG-GCTACACTGTTAATTTT-3'), and human DNA (10 ng/50 µl).

Thermal cycling profile was the following: 95° C.—4 min; (95° C.—0.5 min, 50° C.—0.5 min, 72° C.—1 min)—30 cycles; 72° C.—7 min.

Example 9

Effect of $Mg^{2+}$ on activity of Taq DNA polymerase modified with N-ethoxycarbonyl-2,3-dimethylmaleinimide Activity of the modified DNA polymerase in PCR was determined as described in the Example 8. A set of PCR reactions was carried out in the reaction buffer (see Example 7) supplemented with the following $Mg^{2+}$ concentrations: 1 mM, 1.5 mM, 2 mM, 2.5 mM, 3 mM, 3.5 mM, 4 mM, 5 mM, 6 mM, 7 mM, and 8 mM.

Example 10

Inactivation of the 5'-3' Exonuclease Activity of Taq DNA Polymerase

The exonuclease activity was determined using the following labeled complementary oligonucleotides: [SEQ ID NO: 3] 5'-ATCCAAGATGGGTGTGCTAGTAGGAT-3' and [SEQ ID NO: 4] 5'-ATCCTACTAGCACACCCATCTTG-GAT-3'. Equal amounts (10 units) of the unmodified enzyme and the modified enzyme were incubated with the oligonucleotide duplexes for 4 hours at 37° C. in 10 µl of reaction buffer. Activity of the unmodified Taq DNA polymerase was tested in the following buffer: 75 mM Tris-HCl (pH 8.8 at 25° C.), 20 mM $(NH_4)SO_4$, 0.01% Tween20, and 2 mM $MgCl_2$, while the buffer composition to test the modified Taq DNA polymerase was the following: 20 mM Tris-HCl (pH 8.3 at 25° C.), 20 mM KCl, 5 mM $(NH_4)SO_4$, and 2 mM $MgCl_2$. Both reaction mixtures were tested either in the presence or in the absence of dNTPs.

Reactions were terminated by addition of 5 µl of a "stop" solution (95% (v/v) formamide and 0.01% bromophenol blue). After heating at 95° C. for 2 minutes, the samples were cooled in ice, and then they were loaded onto 15% denaturing acrylamide gel (29:1 acrylamide/bisacrylamide). Electrophoresis was performed in 89 mM Tris-borate (pH8.3 at 37° C.) supplemented with 2 mM EDTA for one hour at ~50 V/cm. After electrophoresis, the gels were fixed in 10% acetic acid and dried. The gels were analyzed using Cyclone Storage Phosphor System and OptiQuant™ Image Analysis Software.

Example 11

Features of Taq DNA Polymerase Modified with N-Ethoxycarbonyl-2,3-Dimethylmaleinimide Sets of PCR reactions were carried out in the Mastercycle (Eppendorf). The reactions performed using 2 units of both the unmodified and the modified enzymes. Composition of the buffer used in the experiments with the modified Taq DNA polymerase was described in the Example 7. The unmodified Taq DNA was tested in the buffer of the following compositions: 75 mM Tris-HCl (pH 8.8 at 25° C.), 20 mM $(NH_4)SO_4$, 0.01% Tween20. Both buffers were supplemented with 2 mM $MgCl_2$, 0.2 mM dNTP, 0.5 µm of each PCR primer and human DNA (100 ng/50 µl). For amplification of 950 by DNA fragment of the CFTR gene, the same set of PCR primers was used as described in the Example 8. A 400 bp fragment of the insulin gene was amplified with the following set of PCR primers:

```
                                        [SEQ ID NO: 5]
5'-GATGGGCTCTGAGACTIA."TAAAGCC-3'
and

[SEQ ID NO: 6]
5'-GTAGAGAGCTTCCACCAGGTGTG-3'.
```

The components of PCR were mixed at room temperature and the reactions were performed using the following cycling profiles:

1. For the 950 bp amplicon: 95° C.—5 min; (95° C.—0.5 mM, 50° C.—0.5 min, 72° C.—1 min)—40 cycles; 72° C.—7 min.
2. For the 400 bp amplicon: 95° C.—5 min; (95° C.—0.5 min, 65° C.—0.5 min, 72° C.—1 min)—40 cycles; 72° C.—7 min.

After completion of PCR, the samples were mixed with aliquots (10 µl) of the 6× MassRuller™ Loading Dye (Fermentas), and the samples were analyzed by gel electrophoresis in 1.7% agarose. The Gene Ruler™ 100 bp DNA Ladder Plus (Fermentas) was used for evaluation of the amplicon size. Electrophoresis was performed in the TBE buffer (89 mM Tris, 89 mM $H_3BO_3$, and 1 mM EDTA) at 5 V/cm for 75 min. After completion of electrophoresis, gels were stained with ethidium bromide (0.5 µg/ml). Then, gels were destained in MiliQ-quality water for 20 minutes. DNA bands were visualized under UV.

Example 12

Determination of the PCR Threshold Using Different Amounts of the Modified DNA Polymerase of the Invention as Compared with Commercial Taq DNA Polymerases Specifically Designed for the Hot-Start PCR Sets of PCR reactions were carried out in the Mastercycler (Eppendorf). The reactions were carried out with the following amounts of DNA polymerases: 0.3125 activity units, 0.625 activity units, 1.25 activity units, and 2.5 activity units. These sets of PCR were performed under conditions optimal for each DNA polymerase. The buffers for both the modified DNA polymerase of the current invention and the unmodified DNA polymerase were described in the Examples 7 and 11, while the buffers for the commercial DNA polymerases were those recommended by the vendors. All experiments were performed in the presence of 0.2 mM dNTP, 0.5 µM of each primers and human DNA (100 ng/50 µl). The PCR primers for amplification of the CFTR gene were described in the Example 8.

The PCR components were mixed at room temperature and the reaction was carried using the following cycling profile: 95° C.—4 min; (95° C.—0.5 min, 50° C.—0.5 min, 72° C.—1 min)—40 cycles; 72° C.—7 min, with the exception of the experiments with the HotStarTaq DNA polymerase, were 15 min pre-incubation at 95° C. was used, as recommended by the vendor.

The PCR products were analyzed as described in the Example 11.

Example 13

Determination of the Threshold of the Target DNA Amplification with the Modified DNA Polymerase of the Invention as Compared with Commercial Taq DNA Polymerases Specifically Designed for the Hot-Start PCR Amplifications and analysis of reaction products were performed as described in the Example 12. The 1.25 activity units of each polymerase were used in the PCR. The following amounts of human DNA were used as templates in the PCR: 0.1 ng, 1 ng, 10 ng, and 100 ng.

Example 14

Determination of the Threshold of the Thermal Cycles with the Modified DNA Polymerase of the Invention as Compared with Commercial Taq DNA Polymerases Specifically Designed for the Hot-Start PCR Amplifications and analysis of PCR products were performed as described in the Example 12. The 1.25 activity units of each polymerase were used in the PCR. The set of PCR reactions was carried out at 20, 25, 30, 35 and 40 thermal cycles. respectively.

Example 15

Performance in the "Fast PCR" of the Modified DNA Polymerase of the Invention as Compared with Commercial Taq DNA Polymerases Specifically Designed for the Hot-Start PCR Sets of PCR reactions were carried out in the GeneAmp® PCR System 9700 (Applied Biosystems). The reactions were carried out with 1 activity unit of DNA polymerases. These sets of PCR reactions were performed in 20 µl of the buffers optimal for each. DNA polymerase. The buffers for the modified Tag polymerase and the unmodified Taq DNA polymerases were described in the Examples 7 and 11, while the buffers for the commercial DNA polymerases were those recommended by the vendors. The following commercial DNA polymerases were chosen for comparison: the FastStart Taq DNA polymerase (Roche), the AmpliTaq Gold DNA polymerase (Applied Biosystems), and the HotStarTaq DNA polymerase (Qiagen). All experiments were performed in the presence of 0.2 mM dNTP, 0.5 µM of each PCR primer and human DNA (40 ng/20 µl). The following primers were used for amplification of the insulin gene:

```
                                        [SEQ ID NO: 7]
5'-CAAGGTCATCCATGACAACTTTG-3'
and

[SEQ ID NO: 8]
5'-GTCCACCACCCTGTTGCTGTAG-3'.
```

The PCR components were mixed in thin-walled PCR tubes on ice and the 500 bp amplicon was generated using the following reaction profile: 95° C.—30 s; (95° C.—0 s, 62° C.—12 s)—30 cycles; 72° C.—10 s.

The PCR products were analyzed as described in the Example 11.

Example 16

Effect of the PCR Extension Time on the Modified DNA Polymerase of the Current Invention as Compared with Commercially Available DNA Polymerases Amplifications and analysis of PCR products were performed as described in the Example 12. The 1.25 activity units of each polymerase were used in the PCR. The following PCR extension times (6 s, 18 s, and 60 s) were used in these experiments:
1. Profile 1: 95° C.—4 min; (95° C.—0.5 min, 50° C.—0.5 mM, 72° C.—6 s)—40—cycles; 72° C.—7 min.
2. Profile 2: 95° C.—4 min; (95° C.—0.5 min, 50° C.—0.5 min, 72° C.—18 s)—40 cycles; 72° C.—7 min.
3. Profile 3: 95° C.—4 min; (95° C.—0.5 min, 50° C.—0.5 min, 72° C.—1 min)—40 cycles; 72° C.—7 min.

Although the examples above have been described with particular reference to the inactivation of thermostable DNA polymerases, a skilled person will appreciate that the method may be applied to many other thermostable enzymes. The preferred modification targets of the present invention are protein amino groups, mainly the $\epsilon$-$NH_2$ groups of lysine residues. Since such residues are typically found throughout the sequence of many enzymes, the present methods are suitable for reversibly inactivating a wide range of target thermostable enzymes.

The invention claimed is:

1. An enzymatically inactivated derivatized thermostable DNA polymerase obtained by a method comprising reacting a thermostable DNA polymerase with a dicarboxylic acid imide compound of formula I:

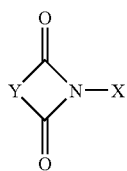

wherein:
X is an electron withdrawing group;
Y is a linker group and represents a radical of formula IIa or IIb:

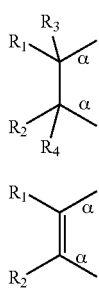

wherein:
$R_1$, $R_2$, $R_3$ and $R_4$ are each independently hydrogen or alkyl, or $R_1$ and $R_2$ together with the carbon atoms to which they are attached form a cycloalkylene, cycloalkenylene, cycloalkyarylene or arylene group; provided that when Y represents a radical of formula IIb at least one of $R_1$ and $R_2$ is alkyl,
and each α is a bond linking the radical to a carbon atom of a carbonyl group shown in formula I;
wherein the linkage to the derivatized thermostable DNA polymerase is at one or more amino groups of the derivatized thermostable DNA polymerase structure and wherein the derivatized thermostable DNA comprises a moiety of formula IIIa or IIIb:

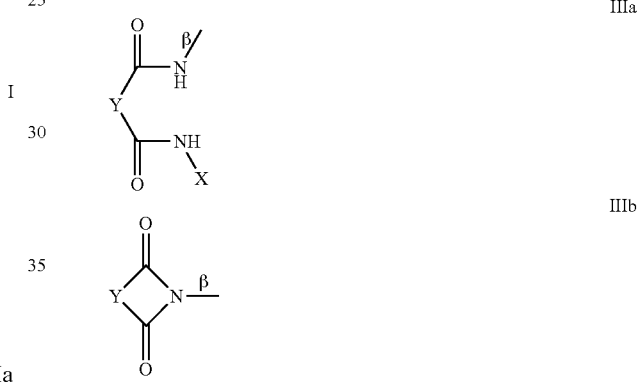

wherein X, Y, $R_1$, $R_2$, $R_3$ and $R_4$ are defined as above and β is a bond linking the moiety to the enzyme;
and
wherein inactivation of the enzymatic activity is reversible and wherein the derivatized thermostable DNA polymerase is stable to heat at 50° C.

2. The derivatized thermostable DNA polymerase according to claim 1 which is derivatised at a ε-amino group of a lysine residue in the DNA polymerase.

3. The derivatized thermostable DNA polymerase according to claim 1 which is derivatised at the α-amino group of an N-terminal amino acid residue of the DNA polymerase.

4. The derivatized thermostable DNA polymerase according to claim 1, wherein X is halogen, hydroxyl, alkoxycarbonyl, alkoxy, acyl or acyloxy.

5. The derivatized thermostable DNA polymerase according to claim 4, wherein the dicarboxylic acid imide is an N-alkoxycarbonyl-2,3-dimethylmaleinimide.

6. A dicarboxylic acid imide-derivatised thermostable DNA polymerase wherein the enzymatic activity of the derivatised DNA polymerase is at least partially inactivated and the inactivation is reversible, wherein the derivatized thermostable DNA polymerase is derivatised at one or more amino groups of the derivatized thermostable DNA polymerase and wherein the derivatised thermostable DNA polymerase comprises a moiety of formula IIIa or IIIb:

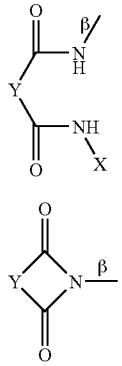

IIIa

IIIb

X is an electron withdrawing group;
Y is a linker group and represents a radical of formula IIa or IIb:

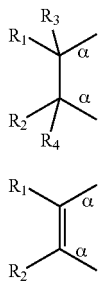

IIa

IIb wherein:
R$_1$, R$_2$, R$_3$ and R$_4$ are each independently hydrogen or alkyl, or R$_1$ and R$_2$ together with the carbon atoms to which they are attached form a cycloalkylene, cycloalkenylene, cycloalkyarylene or arylene group; provided that when Y represents a radical of formula IIb at least one of R$_1$ and R$_2$ is alkyl,
and each α is a bond linking the radical to a carbon atom of a carbonyl group shown in formula I;
β is a bond linking the moiety to the DNA polymerase; and
wherein the derivatized thermostable DNA polymerase is one which is stable to heat at 50° C., wherein the enzymatic activity of the derivatised thermostable DNA polymerase is at least 50% lower than the enzymatic activity of a corresponding underivatised thermostable DNA polymerase, and wherein inactivation of the derivatized thermostable DNA polymerase is capable of being reversed by heating or changing the pH of a medium comprising the derivatized thermostable DNA polymerase.

7. The derivatized thermostable DNA polymerase as defined in claim 6, wherein the DNA polymerase is derivatised at a ε-amino group in a lysine residue of the DNA polymerase.

8. The derivatized thermostable DNA polymerase as defined in claim 7, wherein the DNA polymerase comprises a derivatised lysine residue of formula IVa or IVb:

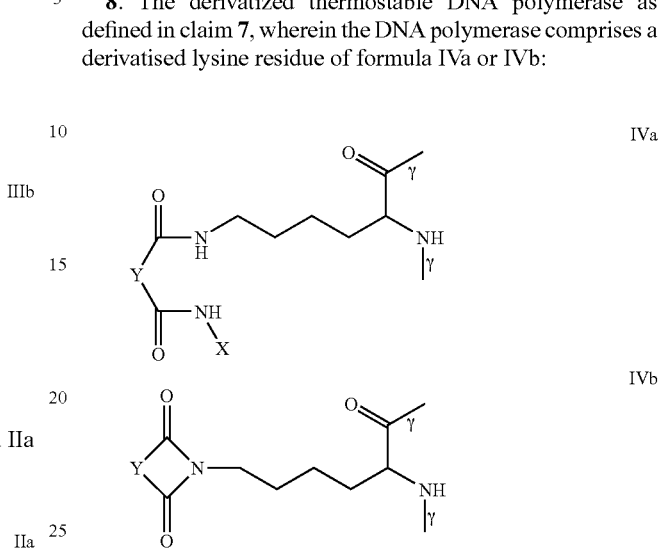

IVa

IVb wherein each γ is a peptide bond linking the derivatised residue to an adjacent amino acid residue in a polypeptide chain of the DNA polymerase.

9. The derivatized thermostable DNA polymerase as defined in claim 6, wherein the DNA polymerase is derivatised at the α-amino group of an N-terminal amino acid residue in the DNA polymerase.

10. The derivatized thermostable DNA polymerase as defined in claim 6, wherein the DNA polymerase is derivatised at an amino acid residue involved in enzymatic catalysis, substrate recognition or determining structural conformation of the DNA polymerase.

11. The derivatized thermostable DNA polymerase as defined in claim 6, wherein the DNA polymerase is derivatised at an amino acid residue located at the active site of the DNA polymerase.

12. An enzyme as defined in claim 6, wherein activity of the derivatised enzyme is at least 70% lower than activity of an underivatised enzyme.

13. The derivatized thermostable DNA polymerase according to claim 6, wherein X is halogen, hydroxyl, alkoxycarbonyl, alkoxy, acyl or acyloxy.

14. The derivatized thermostable DNA polymerase according to claim 13, wherein the dicarboxylic acid imide is an N-alkoxycarbonyl-2,3-dimethylmaleinimide.

15. The derivatized thermostable DNA polymerase according to claim 6, wherein the polymerase is Taq DNA polymerase or Pfu DNA polymerase.

* * * * *

```
SEQUENCE LISTING

<160> NUMBER OF SEQ ID NOS: 8

<210> SEQ ID NO 1
<211> LENGTH: 20
<212> TYPE: DNA
<213> ORGANISM: Homo sapiens

<400> SEQUENCE: 1
gctgcatcat ataagttgcc                                               20

<210> SEQ ID NO 2
<211> LENGTH: 20
<212> TYPE: DNA
<213> ORGANISM: Homo sapiens

<400> SEQUENCE: 2
aaggctacac tgttaatttt                                               20

<210> SEQ ID NO 3
<211> LENGTH: 26
<212> TYPE: DNA
<213> ORGANISM: Homo sapiens

<400> SEQUENCE: 3
atccaagatg ggtgtgctag taggat                                        26

<210> SEQ ID NO 4
<211> LENGTH: 26
<212> TYPE: DNA
<213> ORGANISM: Homo sapiens

<400> SEQUENCE: 4
atcctactag cacacccatc ttggat                                        26

<210> SEQ ID NO 5
<211> LENGTH: 24
<212> TYPE: DNA
<213> ORGANISM: Homo sapiens

<400> SEQUENCE: 5
gatgggctct gagactataa agcc                                          24

<210> SEQ ID NO 6
<211> LENGTH: 23
<212> TYPE: DNA
<213> ORGANISM: Homo sapiens

<400> SEQUENCE: 6
gtagagagct tccaccaggt gtg                                           23
```

```
<210> SEQ ID NO 7
<211> LENGTH: 23
<212> TYPE: DNA
<213> ORGANISM: Homo sapiens

<400> SEQUENCE: 7
caaggtcatc catgacaact ttg                                      23

<210> SEQ ID NO 8
<211> LENGTH: 22
<212> TYPE: DNA
<213> ORGANISM: Homo sapiens

<400> SEQUENCE: 8
gtccaccacc ctgttgctgt ag                                       22
```